(12) United States Patent
Huang

(10) Patent No.: US 9,039,182 B2
(45) Date of Patent: May 26, 2015

(54) VIDEO GAME TO MONITOR RETINAL DISEASES

(71) Applicant: ICHECK Health Connection, Inc., Portland, OR (US)

(72) Inventor: David Huang, Portland, OR (US)

(73) Assignee: iCheck Health Connection, Inc., Portland, OR (US)

(*) Notice: Subject to any disclaimer, the term of this patent is extended or adjusted under 35 U.S.C. 154(b) by 259 days.

(21) Appl. No.: 13/683,641

(22) Filed: Nov. 21, 2012

(65) Prior Publication Data

US 2013/0128229 A1 May 23, 2013

Related U.S. Application Data

(60) Provisional application No. 61/562,346, filed on Nov. 21, 2011.

(51) Int. Cl.
| | |
|---|---|
| *A61B 3/02* | (2006.01) |
| *A61B 3/00* | (2006.01) |
| *G06K 9/46* | (2006.01) |
| *A61B 3/028* | (2006.01) |
| *A61B 3/032* | (2006.01) |

(52) U.S. Cl.
CPC ... *G06K 9/46* (2013.01); *A61B 3/02* (2013.01); *A61B 3/0033* (2013.01); *A61B 3/0041* (2013.01); *A61B 3/028* (2013.01); *A61B 3/005* (2013.01); *A61B 3/032* (2013.01)

(58) Field of Classification Search
USPC .................................................. 351/239, 246
See application file for complete search history.

(56) References Cited

U.S. PATENT DOCUMENTS

| | | | |
|---|---|---|---|
| 4,989,968 | A | 2/1991 | Freedman |
| 4,995,717 | A | 2/1991 | Damato |

(Continued)

FOREIGN PATENT DOCUMENTS

| | | |
|---|---|---|
| KR | 100387356 | 8/2003 |
| WO | 2008005848 | 1/2008 |
| WO | 2010132304 | 11/2010 |

OTHER PUBLICATIONS

American Academy of Pediatrics; Red Reflex Examination in Neonates, Infants, and Children; Pediatrics (Journal); Dec. 2008; vol. 122, No. 6; pp. 1401-1404; US.

(Continued)

*Primary Examiner* — Jack Dinh
(74) *Attorney, Agent, or Firm* — Davis Wright Tremaine LLP; George C. Rondeau, Jr.

(57) ABSTRACT

Systems and methods for providing a video game to map macular visual acuity comprising a multiple choice test where the fixation point is ensured by brief simultaneous presentation of both a central and pericentral targets. The game may be implemented on a hardware platform including a video display, a user input device, and a video camera. The camera is used to monitor ambient light level and the distance between the device and the eyes of the test subject. The game serves as a macular acuity perimeter that produces a map of the acuity of an eye that may be compared with normative data. The type of acuity tested is preferably Vernier acuity, but resolution acuity can also be tested. The test results are transmitted to a health care professional by telecommunications means to facilitate the diagnosis or monitoring of age-related macular degeneration or other relevant eye diseases.

59 Claims, 16 Drawing Sheets

(56) References Cited

U.S. PATENT DOCUMENTS

| | | | |
|---|---|---|---|
| 5,502,520 | A | 3/1996 | Cibis et al. |
| 5,565,949 | A | 10/1996 | Kasha, Jr. |
| 5,886,770 | A | 3/1999 | Damato |
| 5,920,375 | A | 7/1999 | Fahle et al. |
| 5,989,194 | A | 11/1999 | Davenport |
| 6,089,715 | A | 7/2000 | Hoover |
| 6,523,954 | B1 | 2/2003 | Kennedy |
| 6,592,223 | B1 | 7/2003 | Stern et al. |
| 6,616,277 | B1 | 9/2003 | Davenport |
| 6,663,242 | B1 | 12/2003 | Davenport |
| 6,808,267 | B2 | 10/2004 | O'Neil et al. |
| 7,287,857 | B2 | 10/2007 | Glaser |
| 7,665,847 | B2 | 2/2010 | Alster et al. |
| 7,878,652 | B2 | 2/2011 | Chen |
| 2003/0020873 | A1 | 1/2003 | Fink et al. |
| 2006/0114414 | A1 | 6/2006 | McGrath et al. |
| 2007/0182928 | A1 | 8/2007 | Sabel |
| 2008/0013047 | A1 | 1/2008 | Todd et al. |
| 2008/0058655 | A1 | 3/2008 | Severns |
| 2009/0059169 | A1 | 3/2009 | Shimizu et al. |
| 2009/0079937 | A1 | 3/2009 | Chen et al. |
| 2009/0079939 | A1 | 3/2009 | Mimura |
| 2009/0153799 | A1 | 6/2009 | Johns |
| 2010/0128222 | A1 | 5/2010 | Donaldson |
| 2010/0128223 | A1 | 5/2010 | Blumenthal et al. |
| 2010/0195051 | A1 | 8/2010 | Murray et al. |
| 2011/0085138 | A1 | 4/2011 | Filar |

OTHER PUBLICATIONS

American Academy of Pediatrics; American Association of Pediatric Ophthalmology and Strabismus, and the American Academy of Ophthalmology; Eye Examination in Infants, Children, and Young Adults by Pediatricians; Pediatrics (Journal); Apr. 2003; vol. 111, No. 4; pp. 902-907; US.

Eventov-Friedman, et al.; The Red Reflex Examination in Neonates: An Efficient Tool for Early Diagnosis of Congenital Ocular Diseases; Imaj (Journal); May 2010; vol. 12; pp. 259-261; Israel.

Roe and Guyton; The Light that Leaks: Bruckner and the Red Reflex; Survey of Ophthalmology; May-Jun. 1984; vol. 28; pp. 665-670; US.

Tongue and Cibis; Brückner Test; Ophthalmology (Journal); 1981; vol. 88, No. 10; pp. 1041-1044; US.

Donahue et al.; Screening for Amblyogenic Factors Using a Volunteer Lay Network and the MTI PhotoScreener; Ophthalmology (Journal); Sep. 2000; vol. 107, No. 9; pp. 1637-1644; US.

Miller et al.; Comparison of Preschool Vision Screening Methods in a Population with a High Prevalence of Astigmatism; IOVS; Apr. 2001; vol. 42, No. 5; pp. 917-924; US.

Donahue et al.; Sensitivity of Photoscreening to Detect High-Magnitude Amblyogenic Factors; Journal of AAPOS; Apr. 2002; vol. 6, No. 2; pp. 86-91; US.

Chen et al.; Simulation of Eccentric Photorefraction Images; Optics Express; Mar.-Jun. 2003; vol. 11, No. 14; pp. 1628-1642; US.

Donahue et al.; Preschool Vision Screenings: what Should We be Detecting and How Should We Report It? Uniform Guidelines for Reporting Results of Preschool Vision Screening Studies; Journal of AAPOS; Oct. 2003; vol. 7, No. 5; pp. 314-316; US.

Kovtoun et al.; Calibration of Photoscreeners for Single-Subject, Contract-Induced Hyperopic Anisometropia; Journal of Pediatric Ophthalmology & Strabismus; May/Jun. 2004; vol. 41, No. 3; pp. 150-158; US.

Matta et al.; Comparison Between the PlusoptiX and MTI Photoscreeners; Arch Ophthalmol; Dec. 2009; vol. 127, No. 12; pp. 1591-1595; US.

Li et al.; The Detection of Simulated Retinoblastoma by Using Red-Reflex Testing; Pediatrics (Journal); Jul. 2010; vol. 126, No. 1; pp. 201-208; US.

Donahue et al.; US Preventive Services Task Force Vision Screening Recommendations; Pediatrics (Journal); Mar. 2011; vol. 127, No. 3; pp. 568-571; US.

Arnold et al.; Calibration and Validation of 9 Objective Vision Screeners with Contact-Lens Induced Anisometropia; Pediatric Ophthalmology and Strabismus; Mar. 2012; pp. 1-18; US.

Kaakinen, Kari; A Simple Method for Screening of Children with Strabismus, Anisometropia or Ametropia by Simultaneous Photography of the Corneal and the Fundus Reflexes; ACTA Ophthalmologica; Jun. 1978; vol. 57 1979; pp. 161-171; Finland.

Ellis, C.J.K.; The Pupillary Light Reflex in Normal Subjects; British Journal of Ophthalmology; 1981; vol. 65; pp. 754-759; London.

Bobier et al.; Eccentric Photorefraction: Optical Analysis and Empirical Measures; American Journal of Optometry and Physiological Optics; Feb. 1984; vol. 62, No. 9; pp. 614-620; US.

Howland et al.; Optics of Photoretinoscopy: Results from Ray Tracing; American Journal of Optometry and Physiological Optics; Feb. 1985; vol. 62, No. 9; pp. 621-625; US.

Brodie, Scott E.; Photographic Calibration of the Hirschberg Test; Investigative Ophthalmology & Visual Science; Apr. 1987; vol. 28, No. 4; pp. 736-742; US.

Campbell et al.; Effect of Monochromatic Aberrations on Photorefractive Patterns; Journal of the Optical Society of America; Aug. 1995; vol. 12, No. 8; pp. 1637-1646; Canada.

Bobier, W.R.; Geometrical Theory to Predict Eccentric Photorefraction Intensity Profiles in the Human Eye; Journal of the Optical Society of America; Aug. 1995; vol. 12, No. 8; pp. 1647-1656; Canada.

Bobier, W.R.; Slope-Based Eccentric Photorefraction: Theoretical Analysis of Different Light Source Configurations and Effects of Ocular Aberrations; Journal of the Optical Society of America; Oct. 1997; vol. 14, No. 10; pp. 2547-2556; Canada.

http://www.visionrx.com/gcheck/Register.asp?frombc=1, webpage print, 2012.

http://www.testvision.org/decide.html, webpage print, 2012.

U.S. Appl. No. 13/720,182, filed Dec. 19, 2012, Huang et al.

U.S. Appl. No. 13/605,312, filed Sep. 6, 2012, Huang.

International Search Report, PCT/US2012/053951 filed Sep. 6, 2012. Mailed Feb. 28, 2013.

International Search Report mailed Mar. 4, 2013, PCT/US2012/066387 filed Nov. 21, 2012.

Preferential Hyperacuity Perimeter (PHP) Research Group; "Results of a Multicenter Clinical Trial to Evaluate the Preferential Hyperacuity Perimeter for Detection of Age-Related Macular Degeneration"; The Journal of Retina and Vitreous Diseases; 2005; pp. 296-303; vol. 25, No. 3; Tel-Aviv, Israel.

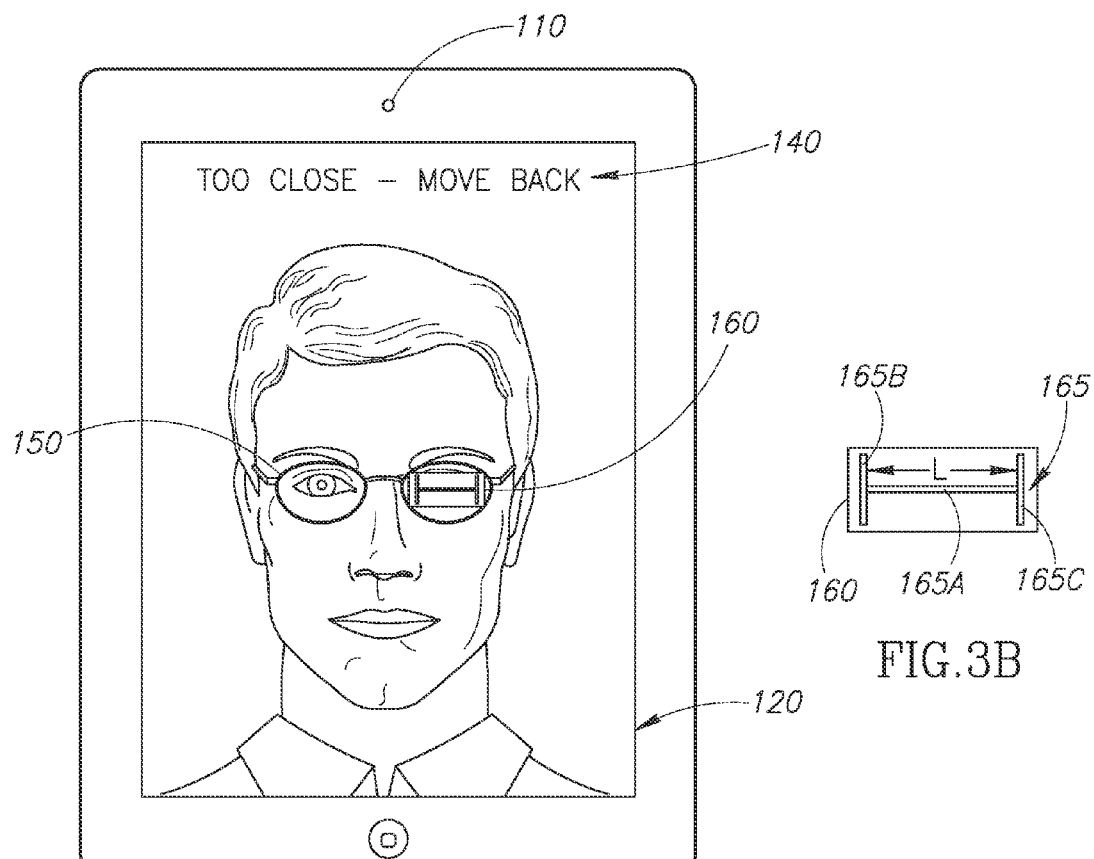

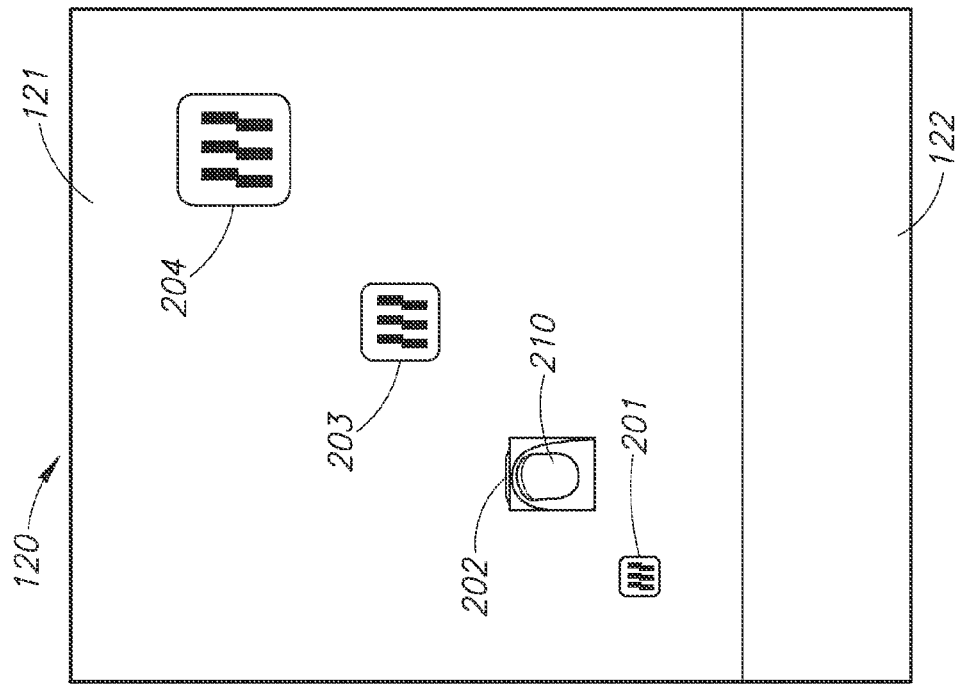
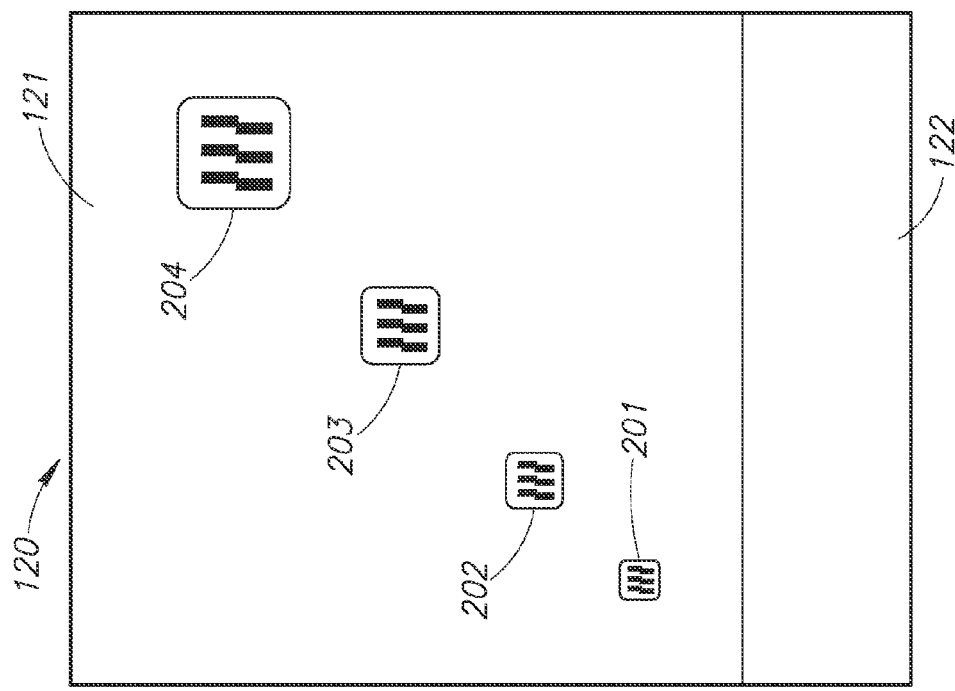

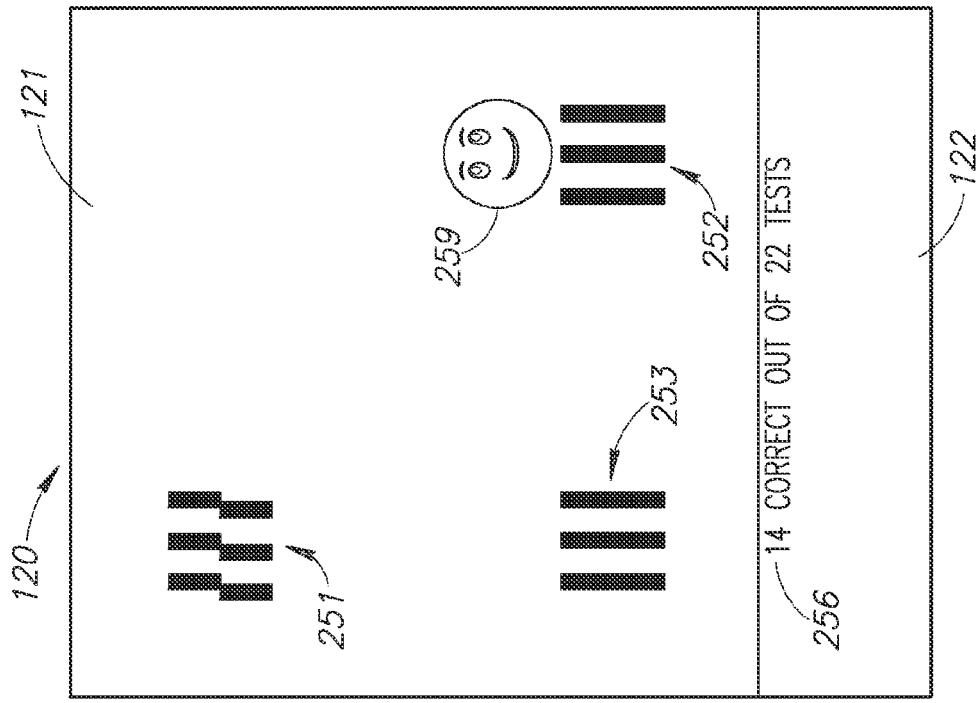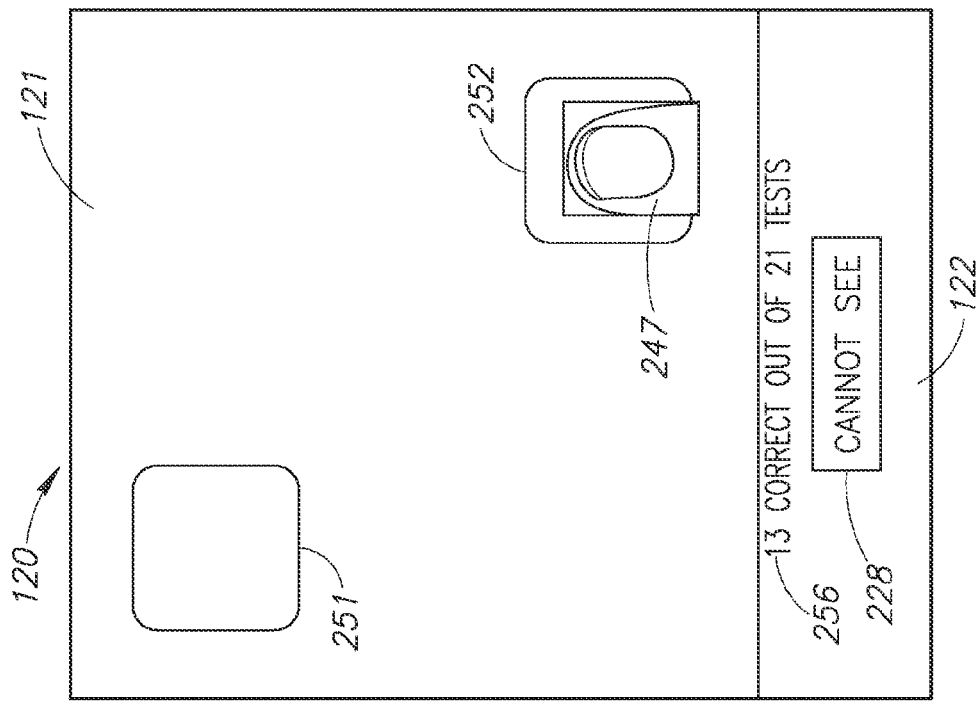

VIDEO GAME TO MONITOR RETINAL DISEASES

BACKGROUND OF THE INVENTION

1. Field of the Invention

The present invention is directed generally to systems and methods for monitoring retinal diseases, and more particularly to providing programs or video games for testing or mapping macular visual acuity.

2. Description of the Related Art

Age-related macular degeneration (AMD) is the leading cause of blindness in the United States and many other industrialized countries. AMD is a degeneration of the macula (central portion of the retina) that is associated with age. The progress of AMD is generally slow in the dry (nonexudative) form of the disease. However, in a portion of affected eyes, the wet (exudative) form of the disease can arise, where abnormal growth of new blood vessels and scar tissue under the retina can lead to rapid loss of vision. The abnormal growth of new blood vessels is called neovascularization, and therefore wet AMD is called neovascular AMD. Fortunately, neovascular AMD can now be treated by intravitreal injection of anti-angiogenic medications, which often stabilize and even reverse the loss of vision. However, early detection of neovascular AMD is needed for treatment to begin in a timely basis and to prevent the loss of vision.

The Amsler chart is a long-standing standard test for AMD that can detect distortions in vision caused by neovascular AMD. However, its sensitivity in detecting neovascular AMD is much lower than a newer test, which is called the preferential hyperacuity perimeter (PHP), wherein the Vernier acuity of the pericentral area is mapped. See Preferential Hyperacuity perimeter (PHP) Research Group. Results of a multicenter clinical trial to evaluate the preferential hyperacuity perimeter for detection of age-related macular degeneration. *Retina* 2005; 25:296-303. The PHP test is taught in U.S. Pat. No. 7,665,847 to Alster et al. Vernier acuity is defined by the resolution with which an eye can detect the relative location of two visual stimuli, such as the relative displacement of two line segments. Vernier acuity is also called "hyperacuity" because its threshold of perception is several times finer than the eye's ability to perceive spatial separation between features in a standard visual acuity target, such as the opening in the Landolt C, line separations in the Tumbling E, or standard optotypes. Compared to normal acuity, Vernier acuity is relatively unaffected by degradation of retinal image quality by cataract and other age-related conditions. Therefore, it is a good test to detect retinal abnormalities in an elderly population.

Currently, PHP testing is performed using a special device. Thus, the inventor has recognized a need for a test for macular visual acuity that may be run on commonly available computing devices with the limits of their available input and output facilities.

BRIEF DESCRIPTION OF THE SEVERAL VIEWS OF THE DRAWINGS

FIG. 3A illustrates the operation of a distance adjustment process using video analysis of a pattern printed onto an eye occluder;

FIG. 3B illustrates an enlarged view of the eye occluder shown in FIG. 3A;

FIG. 5 illustrates a first screen shot of a flash card game measuring central acuity in accordance with an embodiment;

FIG. 6 illustrates a second screen shot of the flash card game measuring central acuity in accordance with an embodiment;

FIG. 19 illustrates a third screen shot of the flash card game measuring perifoveal vision on a small screen in accordance with an embodiment;

FIG. 20 illustrates a fourth screen shot of the flash card game measuring perifoveal vision on a small screen in accordance with an embodiment;

DETAILED DESCRIPTION OF THE INVENTION

Overview

Embodiments of the present invention are useful for the detection and monitoring of retinal diseases affecting primarily the macula. There are many such diseases, but the most common ones are age-related macular degeneration (AMD) and diabetic retinopathy.

Generally, embodiments of the present invention include a video game or program configured to map macular visual acuity comprising a multiple choice test wherein a fixation point is ensured by brief, simultaneous presentation of both a central and pericentral targets. The game is implemented on a hardware platform comprising a video display, a user input device, and an image or video camera. The camera is used to monitor ambient light level, and to monitor the distance between the device and the eyes of the test subject. The game serves as a macular acuity perimeter that produces a map of the acuity of an eye that may be compared with normative data. The type of acuity tested is preferably Vernier acuity (also called "hyperacuity"), but resolution acuity or other types can also be tested.

The test is suitable to be self-administered by the user (also referred to as the player or the subject herein) with or without professional supervision. The results may be transmitted (e.g., wirelessly) to a health care professional by telecommunications means to facilitate the diagnosis or monitoring of age-related macular degeneration or other relevant eye diseases. Embodiments of the present invention are sometimes referred to herein as the macular acuity perimetry (MAP) test.

The Apparatus

Figure 1:
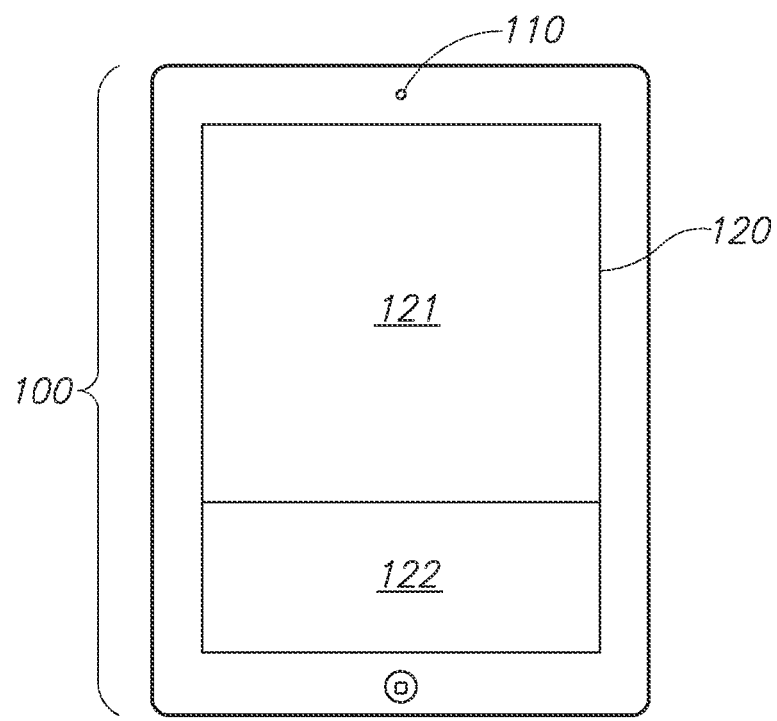
FIG. 1 illustrates a display, input device, and distance-monitoring camera features of an embodiment of the invention implemented using a tablet computer.

Embodiments of the present invention include a computer with a video monitor, a video camera, and a human-user input device. One example of an integrated apparatus serving these functions is the iPad 2® (Apple Inc., Cupertino, Calif.). Other computers or computer systems with similar functionalities may also be used. Referring to FIG. 1, a device 100 is shown that has a video camera 110 configured to monitor the distance between the device and a test subject's eyes. The device 100 also comprises a touch screen display 120 that is divided into a main game play area 121 and an ancillary area 122. The play area 121 is used to display the visual action of a game. The play area 121 is preferably approximately square, but other shapes may also be used. The ancillary area 122 is used as an ancillary human-user input and score display, as discussed below.

Figure 2:
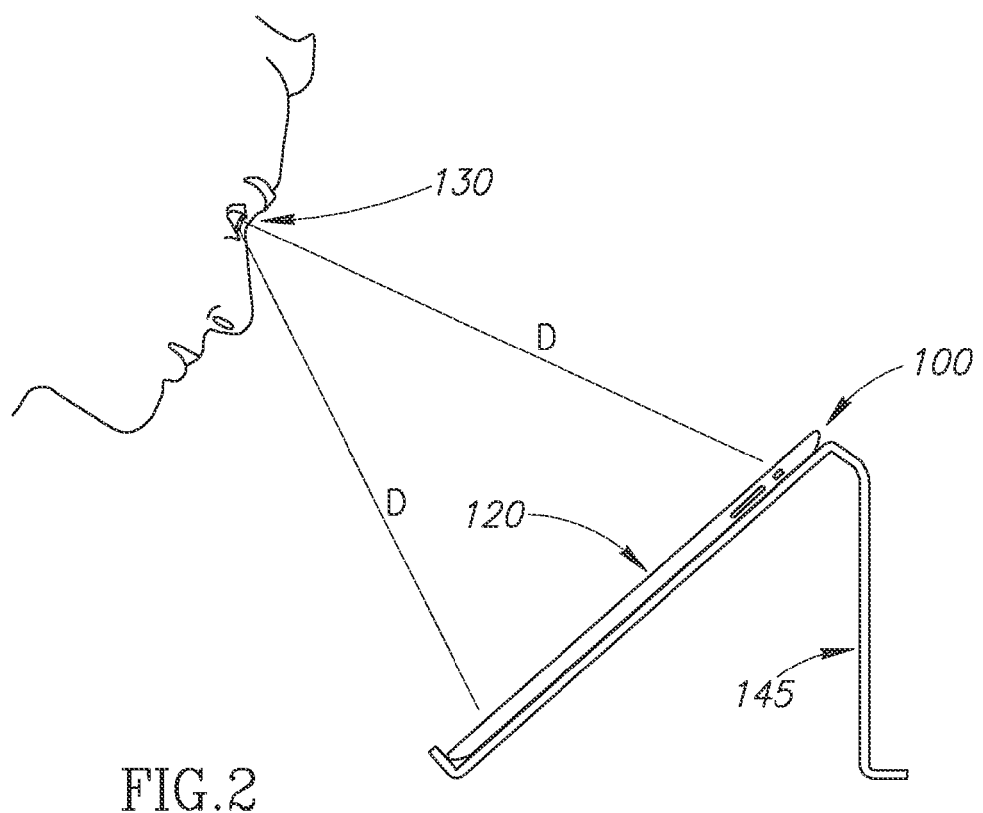
FIG. 2 illustrates the operation of an ambient light monitoring camera and a viewing stand according to an embodiment of the present invention.

Referring to FIG. 2, the device 100 may be positioned on a stand 145 such that the user's eye 130 is approximately equal distance (D) to the top and bottom of the device's display 120. The camera 110 on the front of the device 100 is used to monitor ambient light. The test is preferably performed in dim room lighting (low scotopic). The brightness of the screen 120 may be automatically adjusted according to the ambient light level within an acceptable range. Outside of the acceptable range, a warning message on the screen 120 may be provided to instruct the user to increase or decrease the room lighting appropriately.

Referring to FIGS. 3A and 3B, an occluder 160 is shown that may be used to occlude vision in one eye so the other eye can be tested using the video game of the present invention. The occluder 160 could be mounted on spectacles 150 or could be fixed on the user's head using straps. The occluder 160 has a visible feature 165 of known dimensions which is captured by the video camera 110 and can be analyzed by a computer (see FIG. 4) of the device 100 to monitor the distance between subject's eyes and the device. As shown, the visual feature 165 could include, for example, a horizontal bar 165A with well-defined termination points (e.g., vertical bars 165B and 165C) so that the length of the horizontal bar may be easily determined by computerized automatic image processing. Other shapes or patterns, such as a circle or rectangle, could also be used. Based on the video analysis, the device 100 may display an instruction 140 on the screen 120 (and/or by sound) so the user can position his or her head within the optimal range of distance from the device.

Figure 3C:
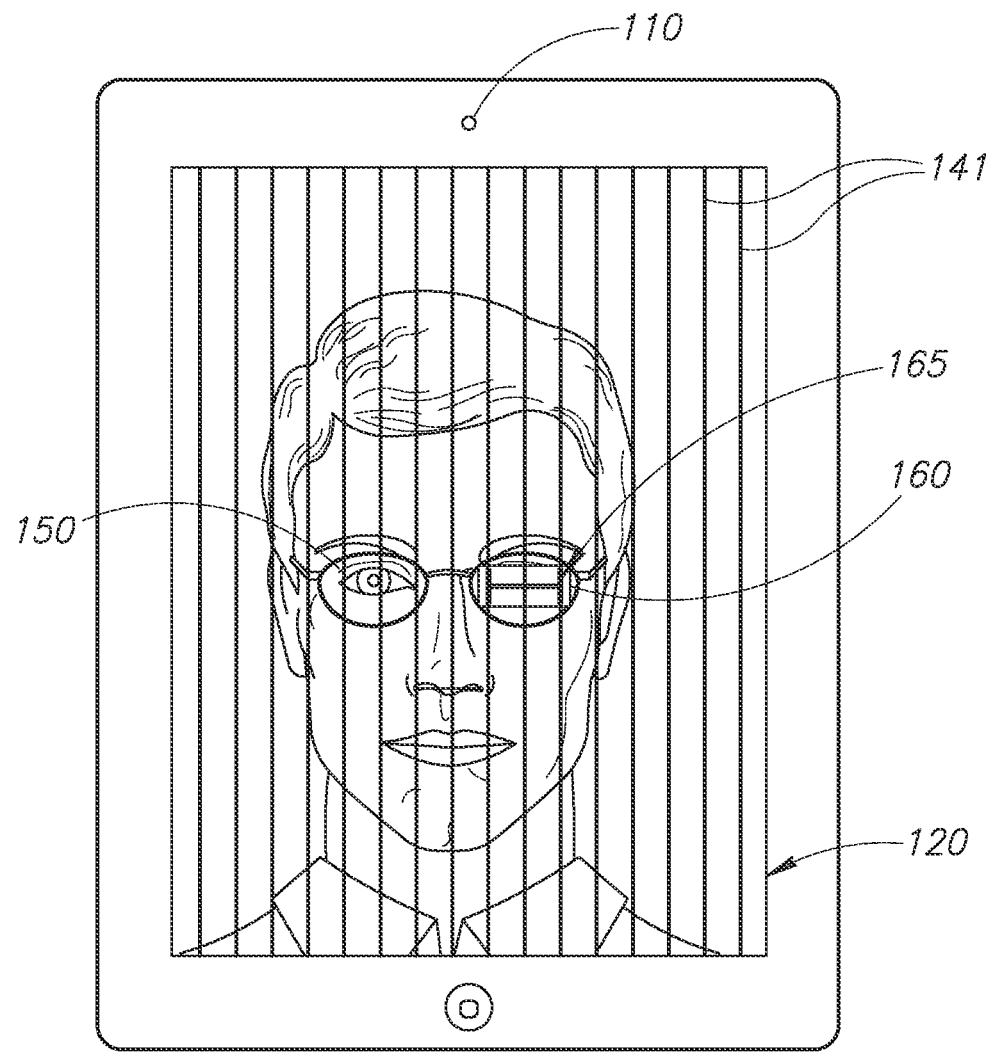
FIG. 3C illustrates the operation of a second distance adjustment process that utilizes a regularly-spaced vertical line overlay.

An alternative method, shown in FIG. 3C, of obtaining the desired viewing distance D asks the user to adjust the viewing distance until the size of the real-time video display the occluder 160 has the correct size. In the example shown, the user compares the video display of the calibration feature 165 against a regularly spaced vertical line overlay 141. The user moves his/her head and/or the device 100 back and forth until the length of the feature 165 (e.g., between vertical bars 165B and 165C) spans two interval spacing between the vertical lines 141.

Another alternative method for the device 100 to monitor viewing distance is to analyze the size of the subject's eye (e.g., corneal width from limbus to limbus) being tested or other features on the subject's face. For this alternative to work, a video frame may first be taken when the user's face is at a known distance from the camera 110. As an example, the distance could initially be established using a measuring tape or ruler with a known length.

Figure 4:
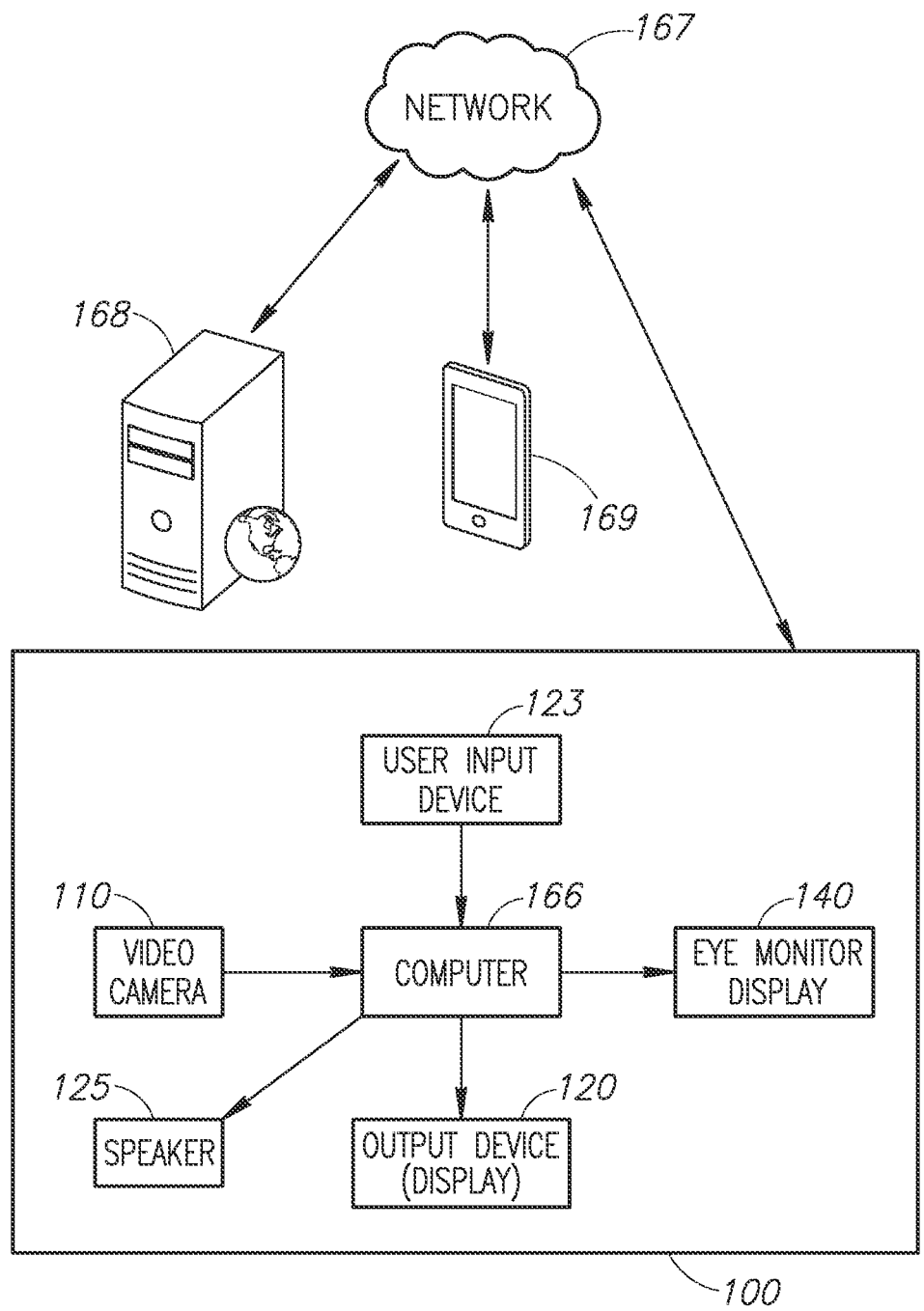
FIG. 4 is a block diagram illustrating the relationship between a computer according to an embodiment and its input and output devices.

Referring now to FIG. 4, an input device 123 and an output device 120 are shown connected to a computer 166 of the device 100. The term computer used in this instance refers to processors, memory, data/control bus, etc., as opposed to the peripheral input and output devices. The input and output functions can both be performed on the same touch screen, as depicted in FIG. 1. The video camera 110 produces image frames that are processed by the computer 166 to monitor the distance between the subject's eyes and the device 100. The subject produces action in the video game with the input device 123 and the game background and actions are displayed on the video display or output device 120. The game sounds are output on a speaker 125.

The test results may be transmitted or uploaded (e.g., wirelessly) to a server 168 over a network 167 (e.g., the Internet, a mobile communications network, etc.). This feature allows for the storage, tracking, review, and analysis of the test results over time to detect patterns, such as the deterioration of a patient's vision. The patient, his or her healthcare professionals, or others may access the data stored on the server 168 through a web browser or via a link to an electronic health record system of a healthcare facility. The test results data may be processed and presented in a manner that is useful for the patient and/or healthcare provider to analyze the results.

The server 168 may also be configured to provide notifications or alerts to the patient or their healthcare provider for any changes in vision that may require further attention or treatment. These alerts may be sent to a patient's and/or healthcare provider's electronic devices (e.g., the mobile phone 169) via email, SMS messages, voice messages, or any other suitable messaging system. For example, if an analysis of the uploaded test results reveals that a patient's vision is deteriorating, the server 168 may automatically send a message to the patient and/or a healthcare provider to alert them of the change in condition. Thus, appropriate action or treatment may be provided.

Initial Setup

The user is instructed to perform the setup steps by the device 100 without the need of human professional instruction and supervision, though a human supervisor could be helpful to assure proper use.

The first time the subject is taking the test, the subject's identifying information (e.g., name, age, etc.) may be entered into the computer 166 using the user input interface 123. An acuity map of a normal population may be used as the initial estimate of the subject's acuity map. For subsequent tests, the initial estimate may be the average of the subject's recent tests.

Since a game is used to perform the MAP test, the terms "game" and "test" are used interchangeably herein. Further, the user of the device 100 is the subject of the MAP test and the game player. Therefore, the terms "user," "subject," and "player" are also used interchangeably.

Before and/or during each game, the brightness of the screen 120 may be adjusted to the desired range by the use of the camera 110 (see FIG. 1) as described above. If the ambient light detected by the camera 110 is too high or low to be compensated for by adjusting the brightness, a message may be displayed on the display area 120 so the user can adjust the light level in the room. The test should generally be administered with the light level in the low scotopic range.

The test is administered at a viewing distance that is sufficient to provide useful AMD diagnostic information. For example, the iPad 2® used in some embodiments has a screen that is 5.8 inches wide. Referring back to FIG. 1, the display area 120 uses this full width of the screen. This provides a maximum perimetry testing area of 18 degrees full width at a viewing distance of 18 inches, using the methods of the current invention. As discussed above, the device 100 monitors the viewing distance D by taking images of the user's face (see FIG. 3) using the camera 110. The computer 166 (see FIG. 4) analyzes the visible feature 165 on the occluder 160 to compute the distance between the camera 110 and the occluder 160, which is approximately the same as the viewing distance. At the setup of each game, the device 100 instructs the user to move his or her head into position so the image of their face (in particular, the occluder 160) can be captured by the camera 110 and displayed in display area 120. The device 100 then instructs the user to move closer to or further from the display area 120 to bring the user's eyes into the target range of viewing distance. The initial target range may be 17 to 19 inches, for example.

Generally, the user should be wearing spectacle correction for their best vision within the operating range of the viewing distance. For an emmetrope, a pair of reading glasses with power of +2.25 D would be optimal for the viewing distance of 18 inches. If spectacles are used, the occluder 160 should be mounted over the spectacle lens over the eye not being tested. If no spectacles are needed or if the subject is using contact lenses, the occluder 160 could be mounted over plano glasses or strapped on as an eye patch.

Game Playing and Perimetry Test Cycle

Many game scenarios could be devised based on the principles of the current invention. For the purpose of demonstration, an exemplary flash card multiple-choice game illustrated in FIGS. 5-20 is described.

The initial rounds of the game are used to establish central visual acuity. This is done using several rounds of "open card" games. Referring to FIG. 5, the display area 120 has a uniform background (e.g., a green background) with a number of open cards 201-204 thereon displaying visual acuity targets over a range of sizes bracketing around the user's estimated central acuity. Vernier acuity targets are preferably used, though normal acuity targets can also be employed. Vernier acuity targets test relative displacements such as relative shifts between two groups of line segments, as shown by the cards 201-204 in FIG. 5. A single line can also be used instead of multiple lines. Other types of unevenness or distortions in a straight line, curve, or circle can also be used. In an opening round, the subject selects the smallest card 201-204 on which he (or she) can perceive the shift between line segments by tapping on the touch screen 120 with a finger 210, as shown in FIG. 6. The visual angle subtended by the spatial shift defines the Vernier acuity.

Figure 7:
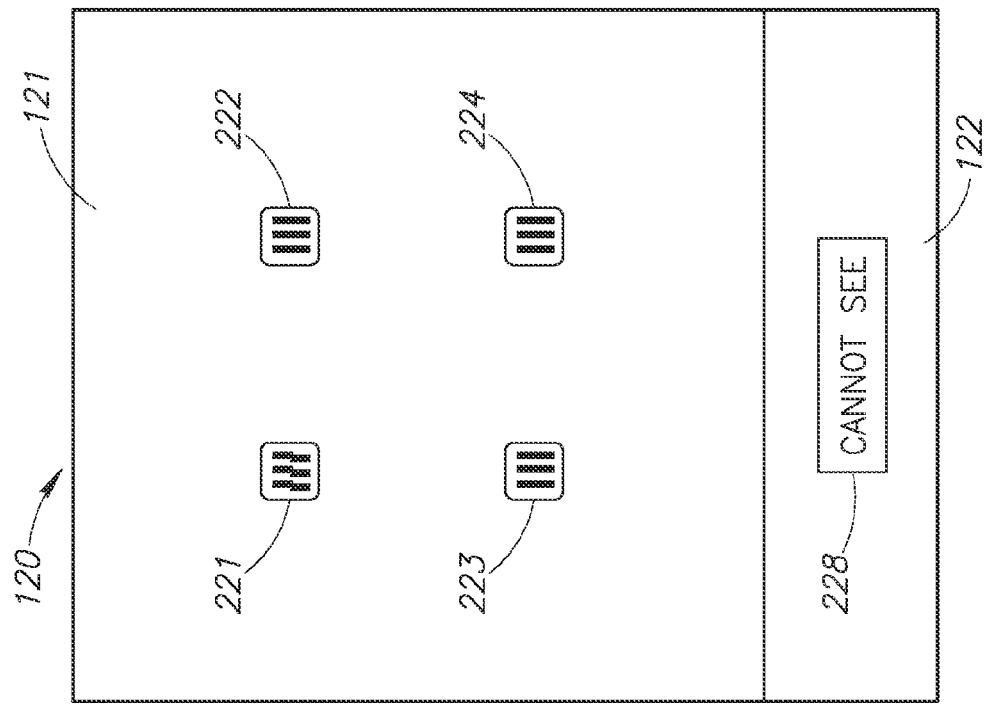
FIG. 7 illustrates a third screen shot of the flash card game measuring central acuity in accordance with an embodiment.

The selected acuity level is then confirmed and refined using a multiple-choice test. Referring to FIG. 7, four open cards 221-224 each showing the same size target are displayed. The player is tasked to select the one card of the cards 221-224 that is different from the other cards. In this example, the card 221 has a lateral shift between the line segments, while the other three cards 222-224 have no shift (aligned). For the sake of brevity, cards with shifted line segments are referred to as "shifted" cards and card with the aligned line segments are referred to as "aligned" cards. The test asks the subject to pick out the one card that is different from the other cards. Thus, the test could involve one shifted card and several aligned cards, or one aligned card and several shifted cards. A greater or smaller numbers of cards (for example, 2, 3, or 9 cards) could also be used.

Figure 8:
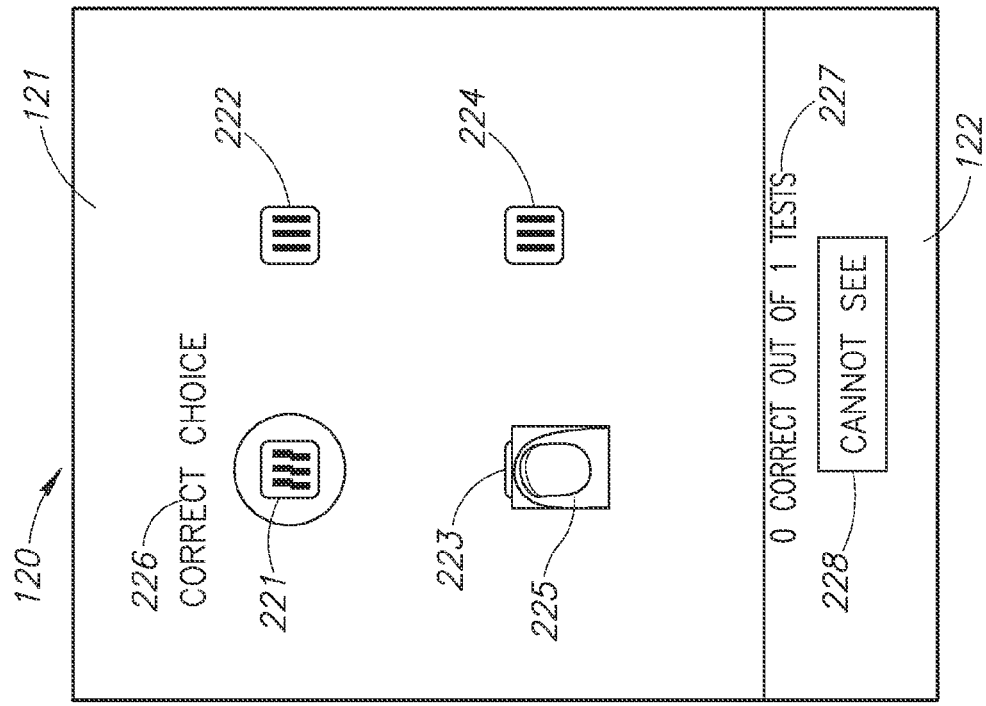
FIG. 8 illustrates a fourth screen shot of the flash card game measuring central acuity in accordance with an embodiment.

Referring to FIG. 8, the subject chooses the one of the card 221-224 he believes is different from the other cards by tapping on the card on the touch screen 120 with a finger 225. In this example, the choice was wrong and therefore the device 100 displays the correct choice with a message 226 and displays a score 227 saying "0 correct out of 1 test." If the subject cannot see the patterns on the card, then the subject should tap on a "cannot see" button 228 rather than tap on the wrong choice. This should be explained in the game instructions so the test may proceed faster. After a brief delay, a new round of the game is started with a display similar to that shown in FIG. 7, but with a new set of cards where the location and type (shifted versus aligned lines) of the correct choice is different (e.g., randomly selected, etc.). In some embodiments, the central acuity level is established when the player chooses a sufficient number of correct cards at a certain error level (e.g., a 5% error level—the probability of achieving equal or greater number of correct choices being less than 5%).

Given a choice of four cards each round and allowing for zero selection error, the subject needs to make the correct choice in three rounds of the game to establish that he was able to perceive the correct choice at the acuity level being displayed. If this occurs, then the acuity level is raised (i.e., the lateral shift is made smaller) and more rounds of games are played until the user's perception is established or refuted. If the player clicks the "cannot see" button 228 (see FIG. 8) or makes the correct choice in only one of three rounds, then perception is refuted. If he make the correct choice in two of three rounds (a borderline case), then one additional round is played for a total of four rounds. If the player makes the correct choice in three of four rounds, then perception is established. If he made the correct choice in two of four rounds, then perception is refuted. Thus for a choice of four cards per round, three rounds are played if the player makes no error and four rounds are played if the player makes one error. For a choice of fewer cards, a larger number of rounds are needed. The numbers of test rounds needed are tabulated in Table 1 shown below.

TABLE 1

The number of test rounds needed to establish perception at <5% error level.

| | # allowed wrong | |
|---|---|---|
| # of choices | 0 | 1 |
| 2 | 5 | 8 |
| 3 | 3 | 5 |
| 4 | 3 | 4 |
| 9 | 2 | 3 |

Table 1 is calculated based on the following equations on the condition that $P_{y \leq Y} < 5\%$.

$$P_c(x) = \frac{n! \left(\frac{1}{c}\right)^x \left(1 - \frac{1}{c}\right)^{n-x}}{x!(n-x)!} \quad \text{Equation 1}$$

$$P_{y \leq Y} = \sum_{x=n-Y}^{n} P_c(x) \quad \text{Equation 2}$$

where $P_C(x)$ is the probability of the number of correct choices being arrived at by random chance, x is the number of rounds in which the correct card was picked, n is the total number of rounds played, c is the number of cards to choose from in each round, $P_{y \leq Y}$ is the probability that y≤Y by random chance, y is the number of rounds in which the wrong card was picked, and Y is the number of wrong choices allowed.

Once the central acuity is established in the initial rounds, the game proceeds to map parafoveal and perifoveal acuity. Anatomically, the fovea refers to the region approximately 1 mm in diameter, the parafovea refers to the surrounding region 2.5 mm (8 degrees) in diameter, and the perifovea the surrounding region 5.5 mm (18 degrees) in diameter. Again, Vernier acuity targets are preferred, but standard acuity targets can also be used. Preferably, a "flash card" game is used.

Figure 10:
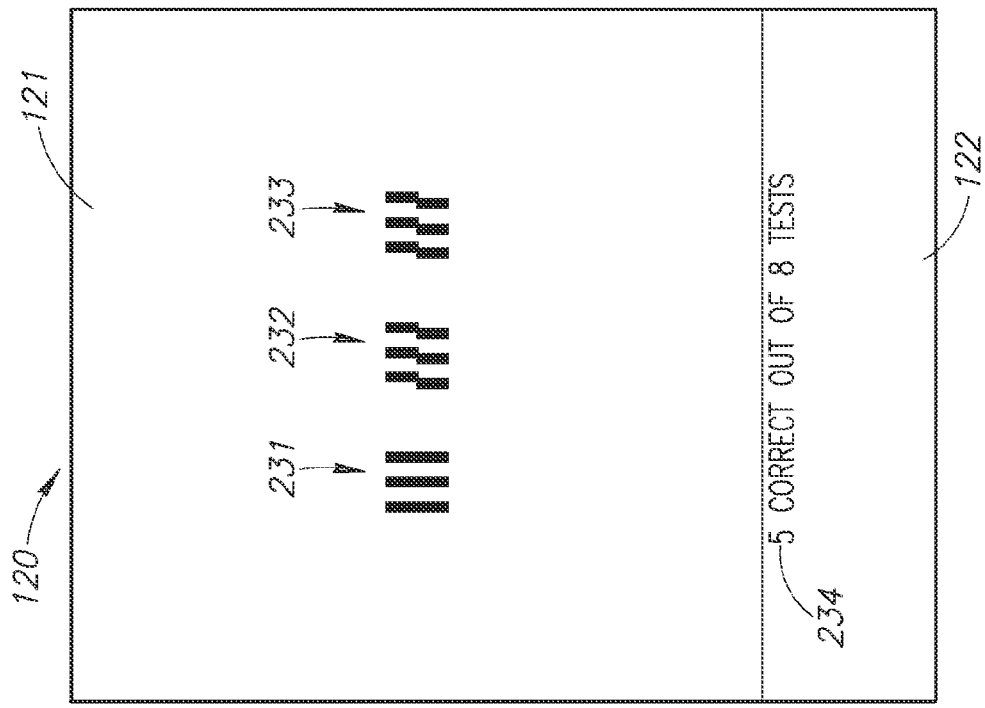
FIG. 10 illustrates a second screen shot of the flash card game measuring parafoveal acuity perimetry in accordance with an embodiment.
Figure 9:
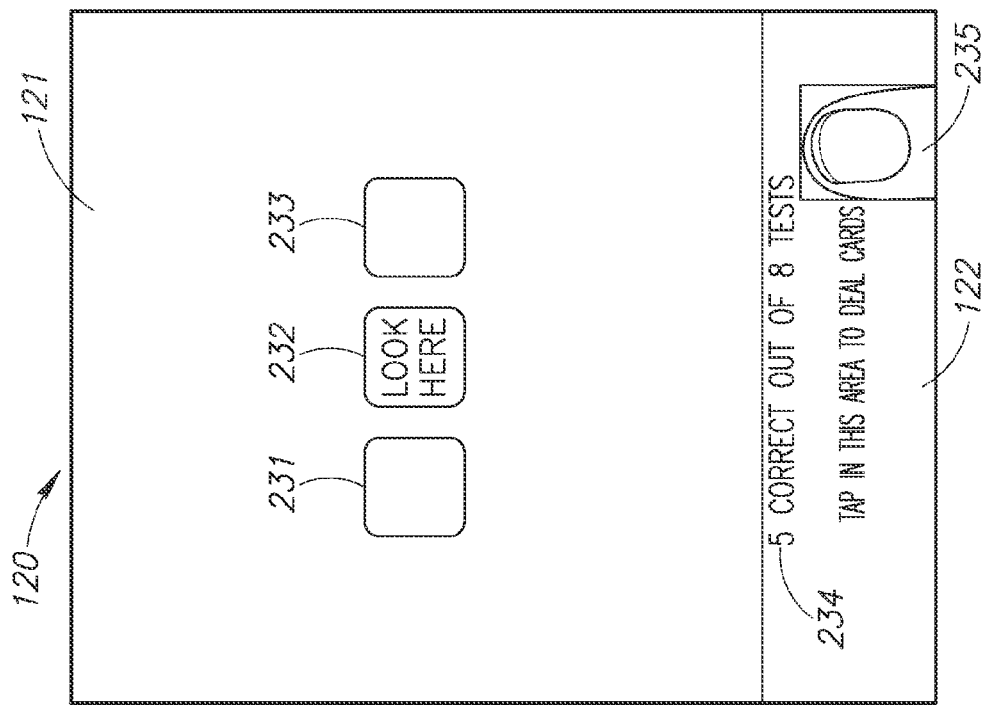
FIG. 9 illustrates a first screen shot of the flash card game measuring parafoveal acuity perimetry in accordance with an embodiment.
Figure 12:
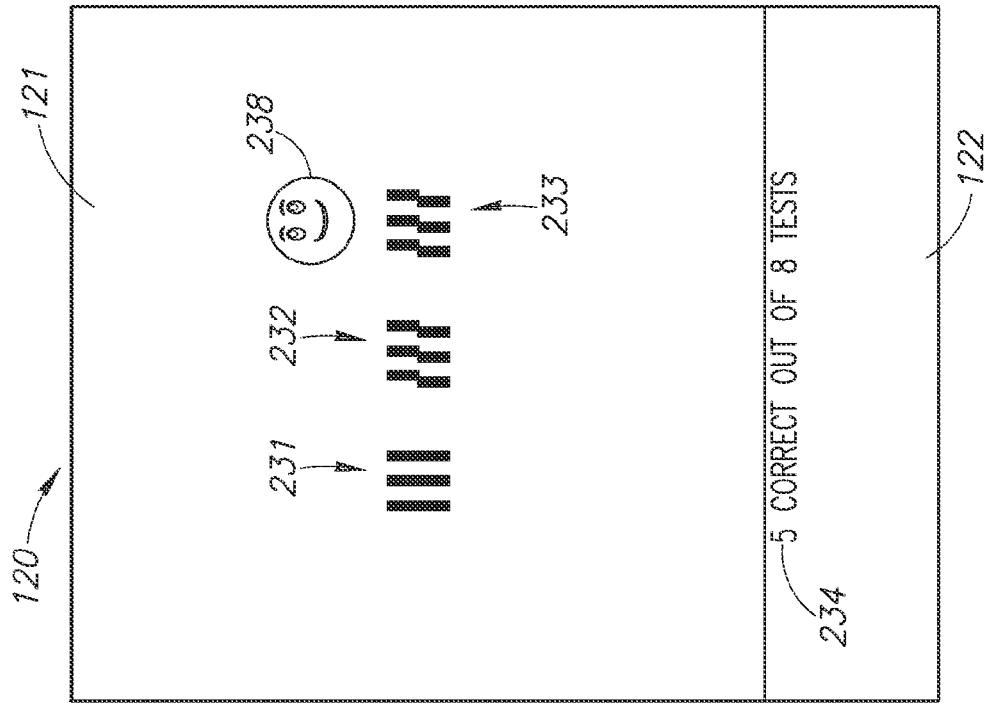
FIG. 12 illustrates a fourth screen shot of the flash card game measuring parafoveal acuity perimetry in accordance with an embodiment.
Figure 11:
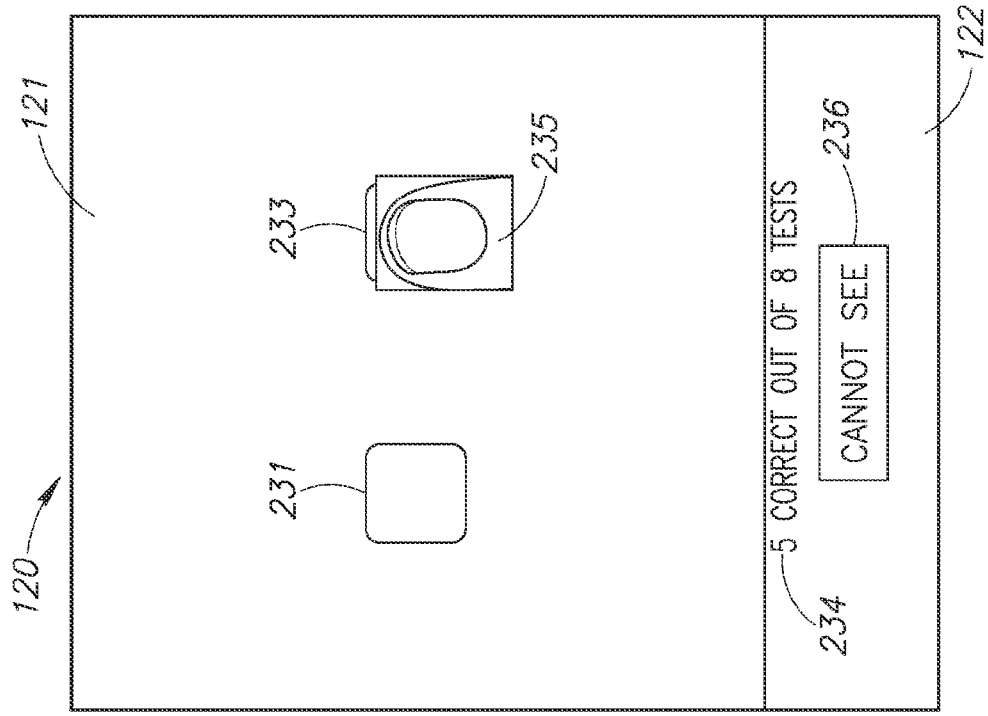
FIG. 11 illustrates a third screen shot of the flash card game measuring parafoveal acuity perimetry in accordance with an embodiment.

An example of parafoveal acuity perimetry is first described. Referring to FIG. 9, three cards 231-233 are dealt face down with their line patterns covered. A game score 234 is shown in the ancillary display area 122 to inform the player of the number of correct choices made and the number of test rounds played. The player activates a "flash reveal" (i.e., a brief display of the face of the cards) of the cards by a finger tap 235 in the display area 122. The player is asked to fixate on the central card 232 at this stage of the game. The "back" of this card may include a "fixation location indicator" (e.g., "look here") to instruct the user to fixate on the central card 232. Referring to FIG. 10, the shifted or aligned line patterns associated with cards 231-233 are revealed in a brief flash (e.g., 0.2 seconds, 0.5 seconds, etc.). The patterns on the faces of the cards 231-233 should be revealed for only a short period of time so the player does not have a chance to shift their gaze from the central card 232 to a side card 231 or 233. After a fraction of a second, the side cards 231 and 233 are once again covered to conceal the line patterns (see FIG. 11). The player is then asked to identify which of the concealed cards 231 and 233 has the same pattern as the central card 232. In this example, the player's finger tap 235 on card 233 is correct. Referring now to FIG. 12, the correct choice of the card 233 is rewarded by a smiley face icon 238 or other visual and/or sound effects. The score 234 is also updated to reflect the increase in the number of correct choices made and the number of rounds played.

Figure 13:
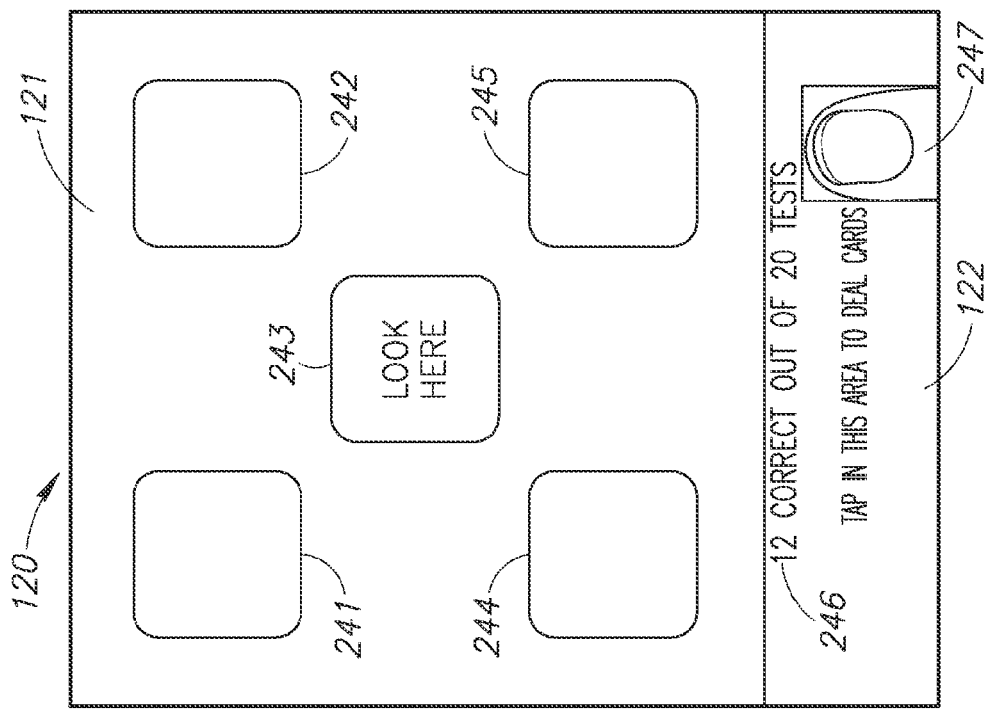
FIG. 13 illustrates a first screen shot of the flash card game measuring perifoveal vision in accordance with an embodiment.

FIGS. 13-16 illustrate one game round to test perifoveal vision. Referring to FIG. 13, five cards 241-245 are dealt face down. A game score 246 is shown in the display area 122 to inform the player of the number of correct choices made and the number of test rounds played. All of the cards 241-245 are dealt with the line patterns covered (i.e., face down). The player activates the flash reveal of the cards by a finger tap 247 in the area 122. The player is asked to fixate on the central card 243 at this stage of the game.

Figure 14:
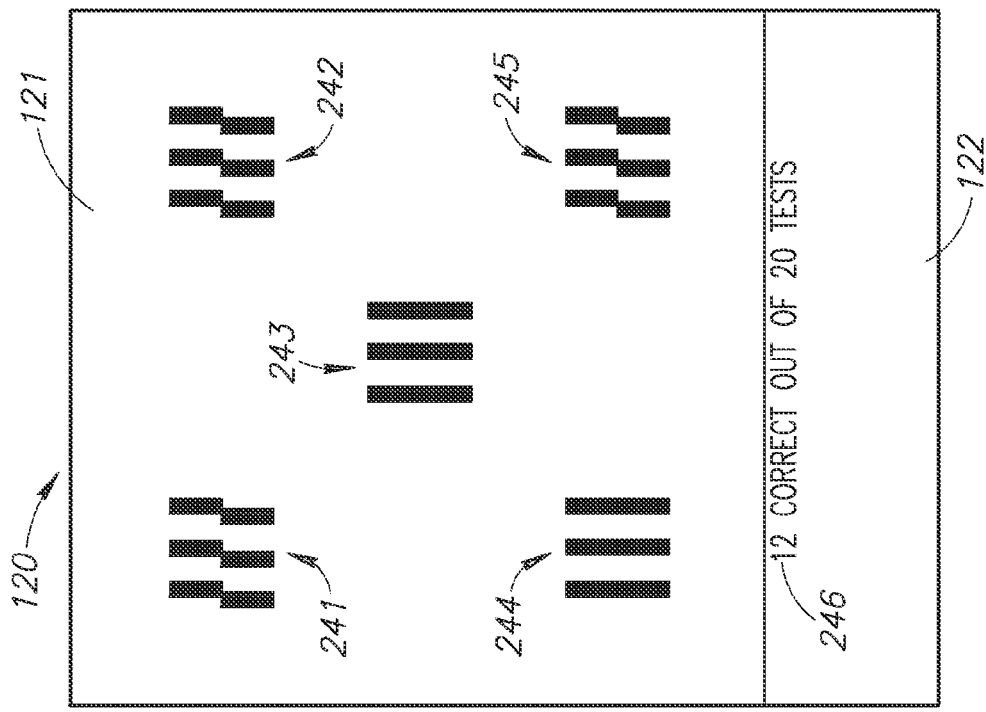
FIG. 14 illustrates a second screen shot of the flash card game measuring perifoveal vision in accordance with an embodiment.
Figure 16:
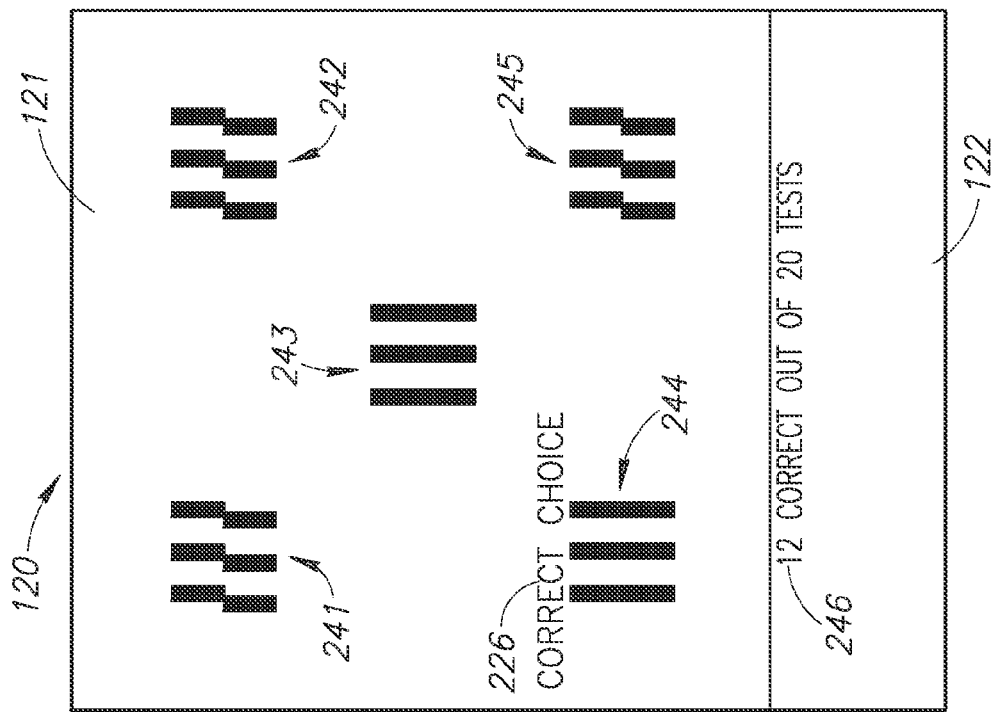
FIG. 16 illustrates a fourth screen shot of the flash card game measuring perifoveal vision in accordance with an embodiment.
Figure 15:
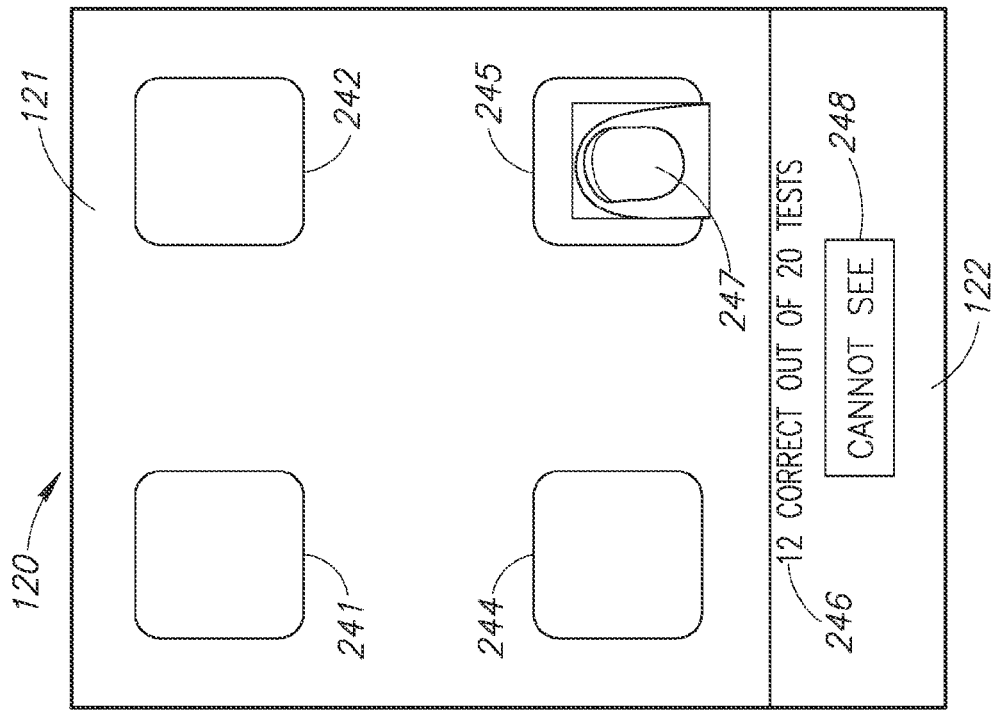
FIG. 15 illustrates a third screen shot of the flash card game measuring perifoveal vision in accordance with an embodiment.

Referring to FIG. 14, the shifted or aligned line patterns associated with cards 241-245 are revealed in a brief flash. After a fraction of a second, the edge or side cards 241, 242, 244, and 245 are again covered to conceal the line patterns (see FIG. 15). The player is then asked to identify which of the concealed cards has the same pattern as the central card 243. In this example, the player's finger tap 247 on the card 245 chooses the incorrect card. Referring now to FIG. 16, the correct card 244 is then revealed and marked as correct by an indicator 226. The score 246 is also updated to reflect the increase in the number of correct choices made and the number of rounds played. Referring back to FIG. 15, the player can make the testing go much quicker by clicking the "Cannot See" button 248 when he is not able to see the patterns on the side cards 241, 242, 244, and 245.

Figure 18:
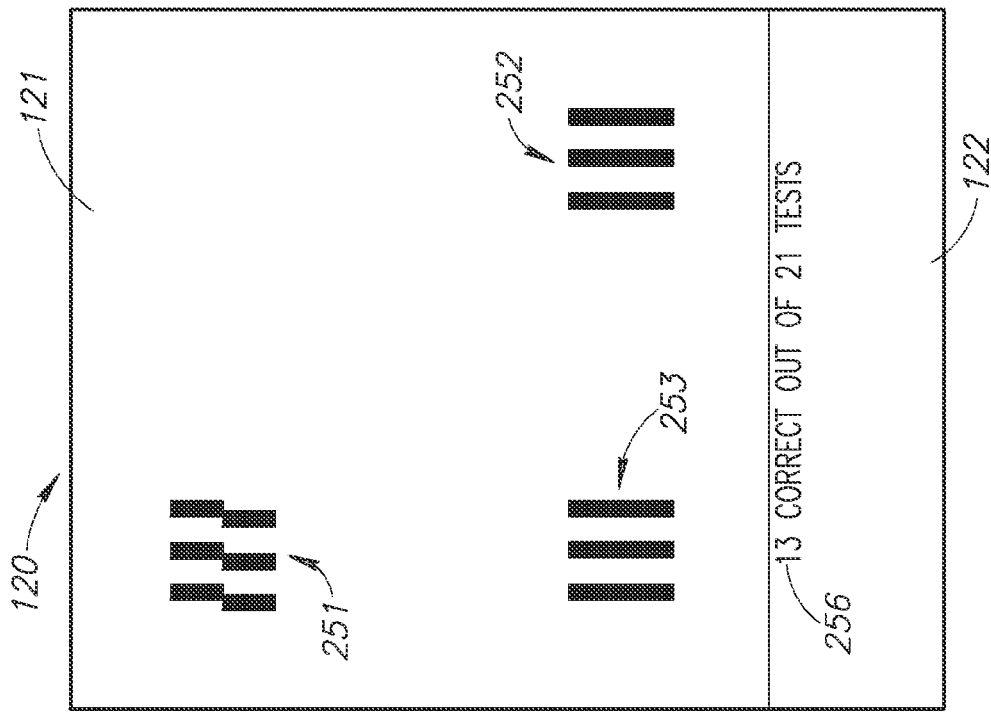
FIG. 18 illustrates a second screen shot of the flash card game measuring perifoveal vision on a small screen in accordance with an embodiment.
Figure 17:
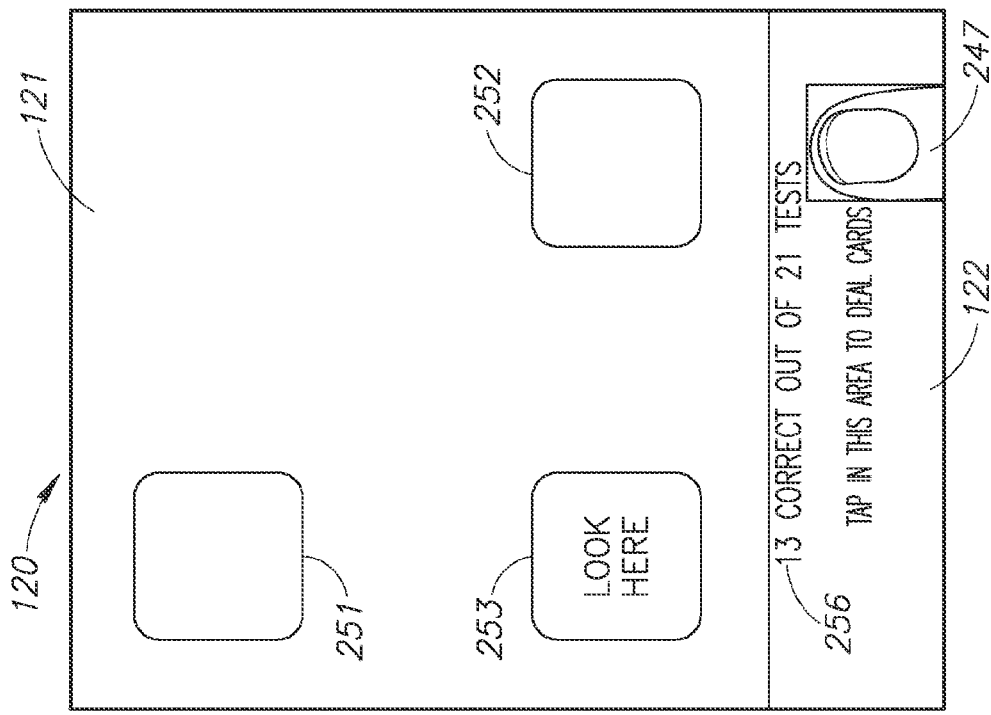
FIG. 17 illustrates a first screen shot of the flash card game measuring perifoveal vision on a small screen in accordance with an embodiment.

FIGS. 17-20 illustrate a method of testing perifoveal vision on a small screen such as on a mobile phone. For example, on a typical mobile phone with a 2 inch screen width, the visual angle subtended by the screen is only 8 degrees, even at a closer viewing distance of 14 inches. If the fixation point is placed at the center of the screen, then the screen is only large enough to test parafoveal vision (8 degrees diameter), but not perifoveal vision (18 degrees diameter). However, the testable visual field can be doubled if the fixation point is placed at the peripheral edge of the display screen. Referring to FIG. 17, the fixation point or "fixation location indicator" is a card 253 located in a corner of the display area 120, with two other cards 251 and 252 positioned at the top-left edge and bottom-right edge, respectively, of the display area 120. As before, the player use the finger tap 247 to briefly reveal the faces of the cards 251-253. Referring to FIG. 18, while fixating on the pattern on the face of the card 253, the player notes patterns 251 and 252 in the perifoveal visual field. Referring to FIG. 19, the player chooses between cards 251 and 252 based on the memory of which card held the same pattern as the fixation card 253. And, as with other embodiments, the player also has the choice of a "cannot see" button 258. In this example, the player chose the correct card 252 and is rewarded with a visual symbol 259 (FIG. 20) and the game score 256 is incremented.

Figure 21:
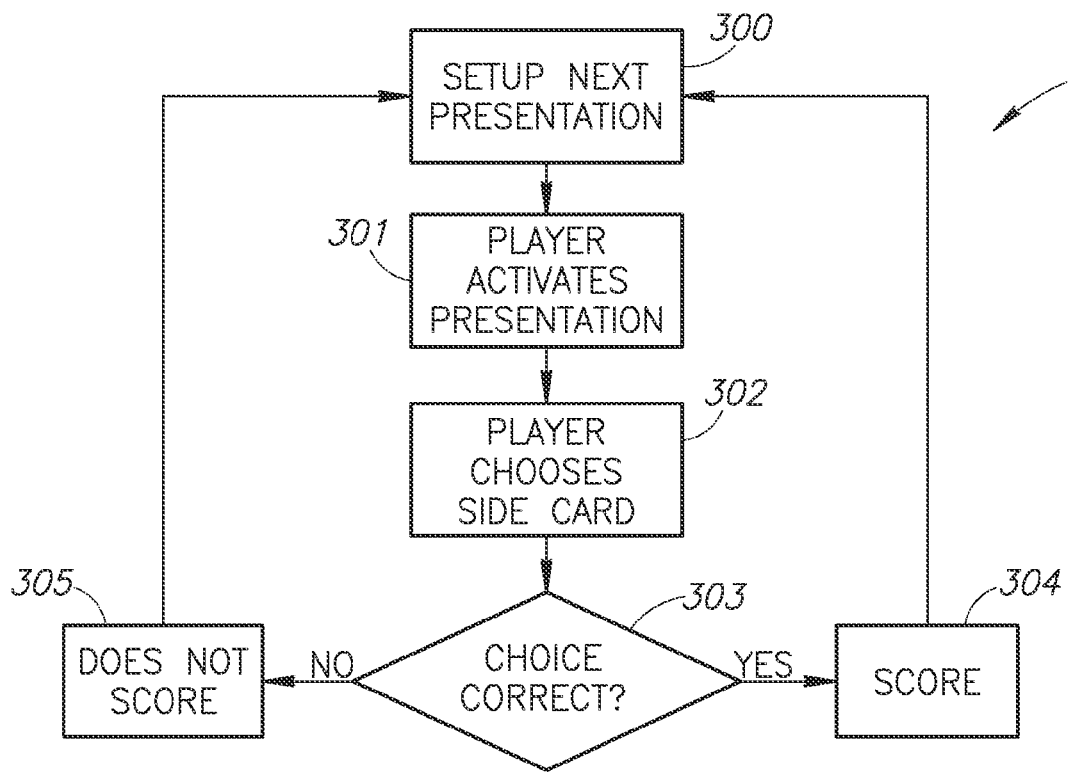
FIG. 21 is a flowchart depicting the logic flow of a cycle of the flash game shown in FIGS. 5-20.

Each round of the flash card game provides one data point on one location in the parafovea or perifovea. The game round can be described by a flow chart (see FIG. 21) for acuity perimetry testing. First, the presentation is set up at 300 by dealing the cards face down. Then, the acuity targets (shifted and aligned line patterns) are presented for a brief moment when the player gives a signal (e.g., a finger tap) to do so at 301. The parafoveal or perifoveal location being tested is the side card with the same line pattern as the central card. The player must choose (e.g., by finger tap) the correct location (or card) at 302. If the choice is correct, decision 303 equals yes, then the score is incremented at 304. If the choice is incorrect, decision 303 equals No, then the score is not incremented at 305. The next round of the game is then played.

Mapping of Stimulus Perception Threshold

One output of the flash game is an acuity perimetry map. The dimension of the map is preferably approximately 16 degrees, which can be easily accommodated by tablet computers currently on the market. For example, the iPad 2® has a display area that is 5.8 inches wide. This provides a maximum visual field width of +/−18 degrees at a viewing distance of 18 inches. With the use of off-center fixation, 16 degrees of testing can be accomplished even on a smart phone screen.

Figure 22:
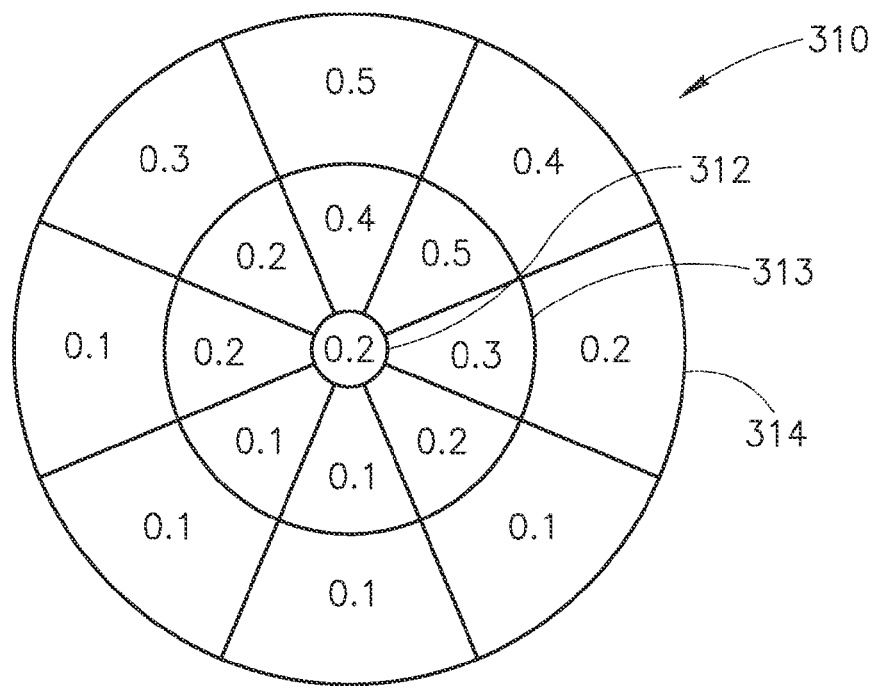
FIG. 22 depicts an exemplary Vernier acuity LogMAR deviation map output from the flash game.

Referring to FIG. 22, an acuity perimetry map 310 is presented as a polar grid of acuity values on the logarithm of minimum angle of resolution (LogMAR) scale. On the LogMAR scale, normal acuity (for the location) has a value of zero. Each ten-fold increase in the size of target needed for threshold perception increases LogMAR by 1.0. A LogMAR of 0.3 indicates that approximately a two-fold increase in target size is needed for threshold perception. Acuity is preferably determined to a precision of 0.1 LogMAR units. For the purpose of AMD screening and monitoring, targets of high contrast are used. The polar grid is divided into a central region 312 spanning the central 3 degrees diameter, parafoveal region 313 spanning the annulus from 3 degrees to 8 degrees diameter, and perifoveal region 314 spanning the annulus from 8 degrees to 16 degrees diameter. The parafoveal and perifoveal annuli are each subdivided into eight sectors. FIG. 22 represents one implementation. More or fewer sectors or annuli could be employed. Rectangular grids could be also be employed instead of a polar grid as well. The map division shown in FIG. 22 may be preferred because the number of test locations (i.e., 17 test locations) is reasonable and the sampling density is appropriately weighed with denser central sampling.

The map 310 is measured over many rounds of the game. The central acuity is tested in the initial rounds of the open card game as described above. The central acuity limits the smallest acuity target that could be used to test parafoveal and perifoveal vision. Then, a series of flash card games are played. The distribution of target locations depends on test location of the number of choices given. For example, a two-choice (two choices of side cards plus one central card=three total cards) game is shown in FIG. 10, where card 233 is the location where acuity is being tested and card 231 is placed in the location opposite the test location, also within the parafoveal annulus. An example of a 4-choice game is shown in FIG. 14, where card 244 is the location of acuity testing and three other cards (241, 242, and 245) are distributed evenly in the perifoveal annulus.

At the beginning of the game, the number of tests at each location can be found in column 2 of Table 1 shown above. For example, for a two-choice game, five tests are needed at each location. Since there are 16 parafoveal and perifoveal test locations (see FIG. 22), a total of 80 flash card rounds are needed. These rounds are randomly ordered into a game sequence and played. At each round, the central target line pattern is randomly assigned to be either aligned or shifted. After the primary flash card rounds, the acuity target at a location is considered to be perceived if it is correctly chosen in all tests (e.g., five out of five times for the two-choice game), and considered not perceived if two or more incorrect choices are made. The test results at some locations could be equivocal (e.g., one error out of five choices), and three more tests are needed at these locations. These secondary flash card rounds are also randomly sequenced and played. After the secondary flash card rounds at each location, the target is considered perceived if only one or less incorrect choice is made, and is considered not perceived if two or more incorrect choices are made. Depending on perception, the target size at each location is then incremented or decremented for the next series of flash card rounds. The game series are played until enough information is accumulated to determine the LogMAR acuity map.

Figure 23:
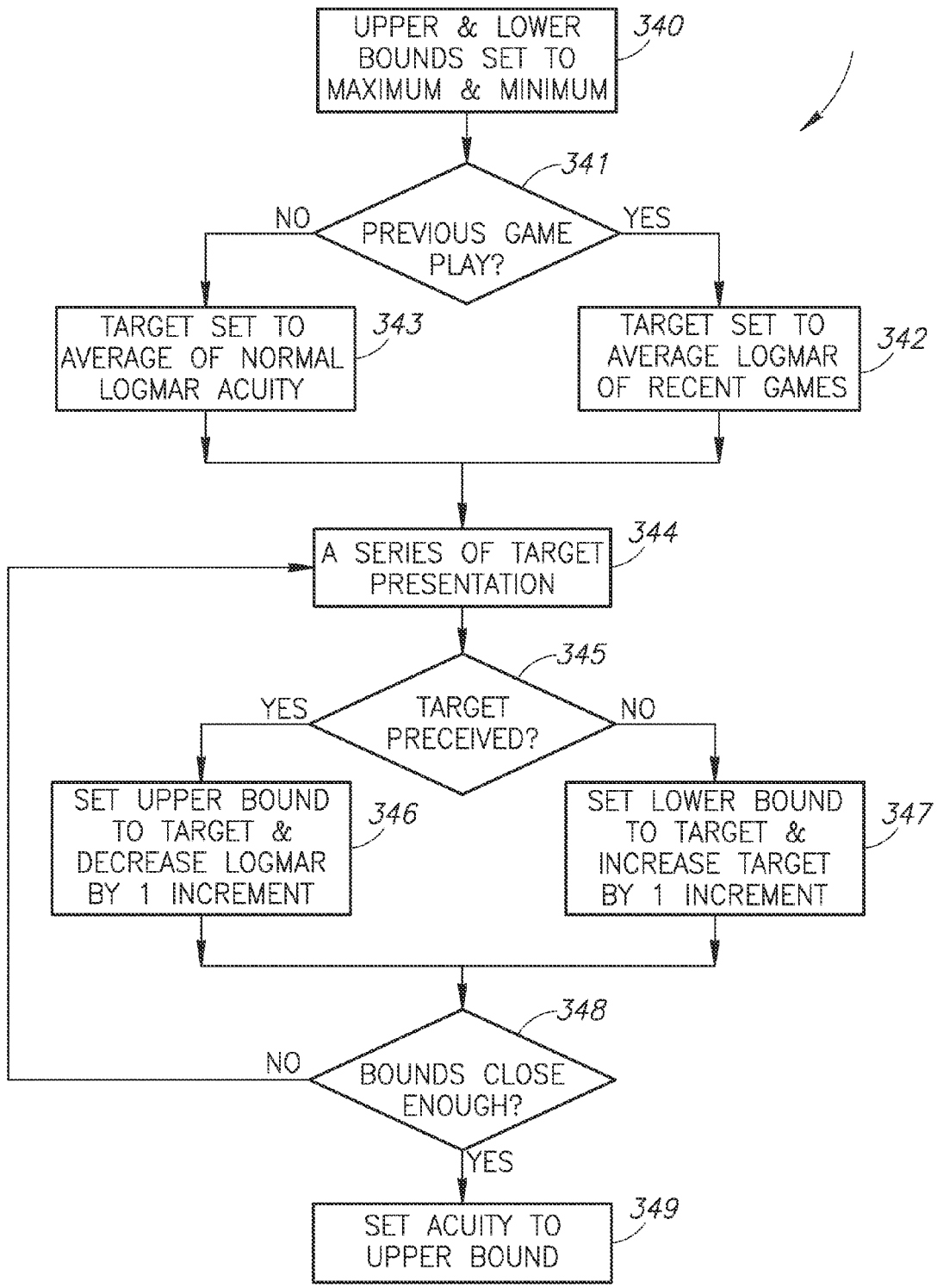
FIG. 23 is a flow chart depicting the testing cycle used to establish the acuity at one visual location.

The series of testing needed to determine LogMAR is determined by an iterative bracketing algorithm. Referring to FIG. 23, the upper and lower bounds of LogMAR acuity at a parafoveal or perifoveal location are initially set to the largest and smallest possible targets at 340. The initial size of the acuity target is set according to a best guess. If the game has been played before, decision 341 equals yes, then the best guess may be the average of recent games at 342. For example, the results of the most recent three games in the past month could be averaged. If no game had been played before, decision 341 equals No, the best guess may be the average LogMAR acuity level at the same test location for a normal reference population.

The target is then presented in a series of flash card games as described above at 344. If the target is perceived, decision 345 equals yes, then the LogMAR upper bound is set to the target size and the target size for the next series of flash card tests is set one increment smaller at 346. The increment of target sizing is preferably 0.1 LogMAR units. If the target is not perceived, decision 345 equals No), then the LogMAR lower bound is set to the target size and the target size for the next series of testing is made one increment larger. If the upper and lower bounds are more than 0.1 LogMAR unit apart, decision 348 equals No, then additional series of game testing are done at the test location at 344 using the new target size. If the upper and lower bounds are only 0.1 LogMAR unit apart or less, decision 348 equals Yes, then no more testing is necessary at the location and the acuity output at the location is set to the upper bound (smallest target shown to be perceived) at 349. Other methods for approaching and determining the threshold value may be used. For example, rather than incrementing or decrementing the target size by 1 increment each interval, the target size may be set half way between the upper bound and lower bound at each interval.

The number of choices in each flash card round should be determined by the ability of the player to rapidly process visual information. This ability will increase as more games are played. Thus, preferably, a two-choice flash card game is played initially, and then the player is given the opportunity to advance to a three-choice game if the score is high. Following this, the player is again given the opportunity to advance to a four-choice game if the score is high. Higher number of choices at each round means fewer rounds are needed (see Table 1 above). This leads to a shorter and more challenging game. However, because the primary purpose of the game is to test retinal function rather than visual processing, the number of choices per round is preferably kept relatively low (e.g., between two and four choices) so mistakes due to inattention are infrequent.

Alternative Test Targets

Figure 24:
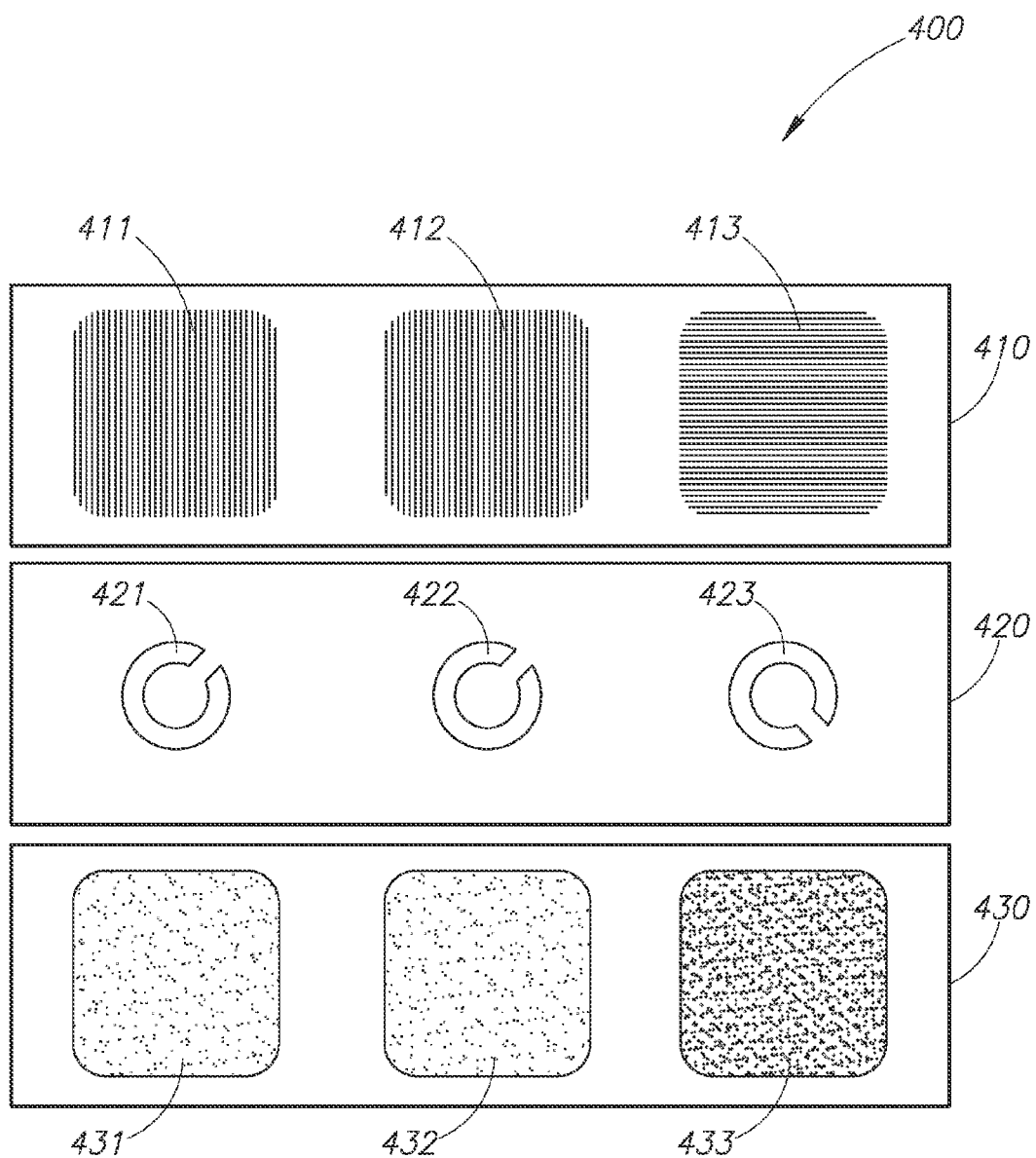
FIG. 24 illustrates alternative resolution acuity testing targets and gray-scale testing targets.

The tests so far illustrated utilized Vernier acuity targets. But it should be appreciated that alternative targets could be used to test different aspects of vision. For example, referring to FIG. 24, the targets could test line orientation 410 (targets 411, 412, and 413), Landolt C orientation 420 (targets 421, 422, and 423), color or gray level 430 (targets 431, 432, and 433 having differing gray levels or color levels), color value or saturation (not shown), commonly used Snellen letter or tumbling E acuity targets (not shown), or other targets could be used.

Advantages

Embodiments of the present invention comprise a video game-based acuity perimetry test that has some or all of the following advantages as well as other advantages:
1) Embodiments of the present invention can be implemented on common consumer-owned hardware platforms such as a smart phone, laptop computer or a tablet computer (e.g., an iPad 2®). This allows more frequent testing by users.
2) The central fixation point is established by forcing the player to know the pattern of the central card. Thus, there is less chance of error due to the player cheating or otherwise shifting central gaze to a peripheral target.
3) For smaller screens, the fixation point is placed off-center to allow testing of perifoveal vision.
4) The video game uses interesting visual stimuli, visual action, and background scenery to help hold a user's attention.
5) The video game uses background music and action-generated sounds to help hold the user's attention.
6) The video game keeps a score related to a user's performance towards goals to help hold the user's attention and motivate repeated playing of the game.
7) The pace of the game is controlled by the player.
8) The distance between the eye being tested and the display screen is established by video imaging of the occluder, obviating the use of a chin rest or other devices to fix the head position relative to the display screen.
9) The ambient light level is monitored by the video camera included in the apparatus of the current invention.

Thus, the present invention provides a "home test" that can be self-administered by subjects who have AMD or are at risk for AMD, so that the test can be performed frequently (e.g., daily or weekly, etc.). The test may be in the form of a game that can maintain player interest. And the resulting macular acuity map may be automatically analyzed by a computer and transmitted electronically to a physician or healthcare provider who monitors the patient's eye health.

Example Hardware Environment

Figure 25:
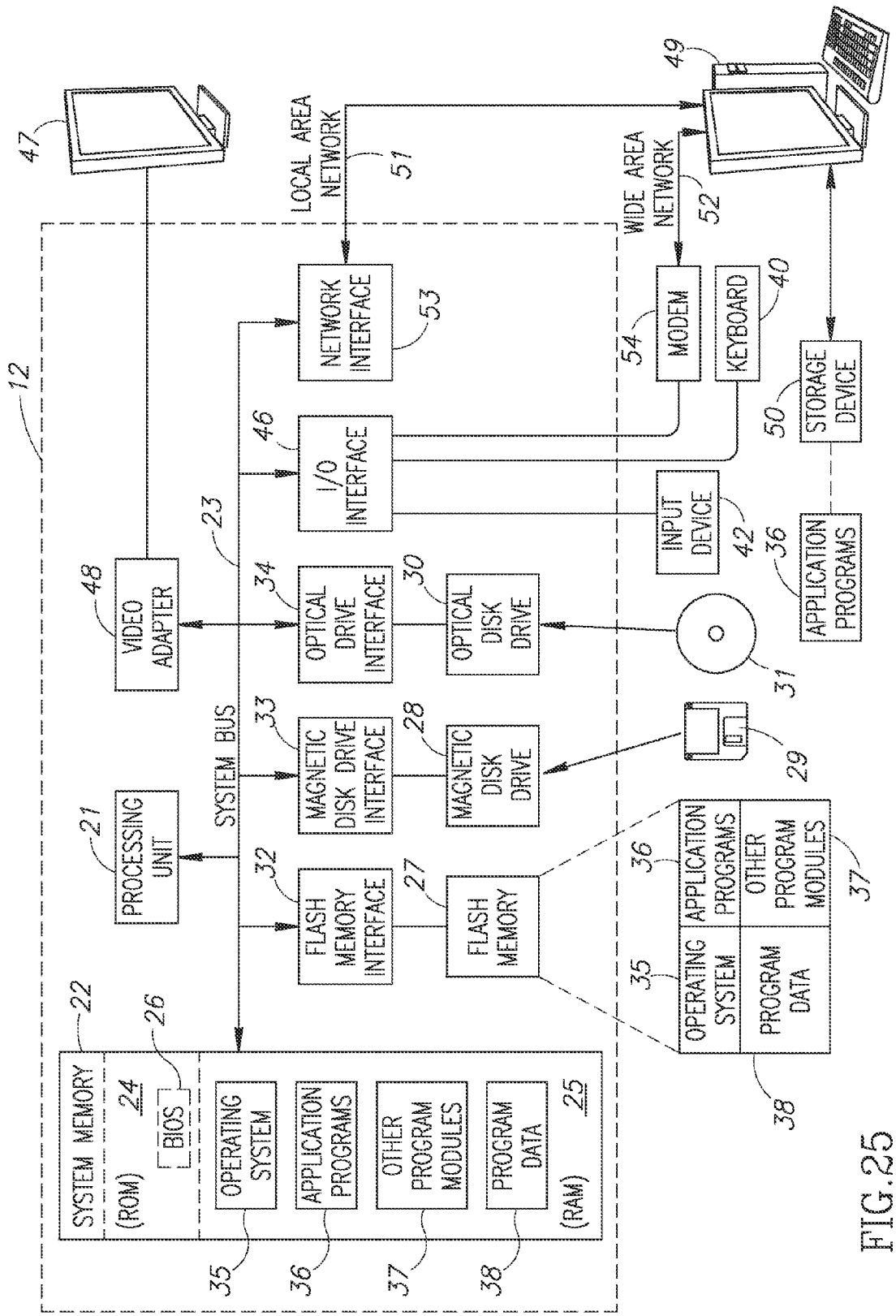
FIG. 25 is a diagram of a hardware environment and an operating environment in which the computing devices of the systems disclosed herein may be implemented.

FIG. 25 is a diagram of hardware and an operating environment in conjunction with which implementations of the device 100 may be practiced. The description of FIG. 25 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multiprocessor systems, microprocessor-based or programmable consumer electronics, network PCs, minicomputers, mainframe computers, tablet computers, smartphones, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 25 includes a general-purpose computing device in the form of a computing device 12. The device 100 may be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like. The computing device 12 may be a tablet computer, a smart phone, a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a flash memory 27, a magnetic disk drive 28 for reading from or writing to a removable magnetic disk 29, and an optical disk drive 30 for reading from or writing to a removable optical disk 31 such as a CD ROM, DVD, or other optical media.

The flash memory 27, magnetic disk drive 28, and optical disk drive 30 are connected to the system bus 23 by a flash memory interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, hard disk drives, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the flash memory 27 and other forms of computer-readable media (e.g., the removable magnetic disk 29, the removable optical disk 31, flash memory cards, hard disk drives, SSD, USB drives, and the like) accessible by the processing unit 21 may be considered components of the system memory 22.

A number of program modules may be stored on the flash memory 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and input device 42. The input device 42 may include touch sensitive devices (e.g., a stylus, touch pad, touch screen, or the like), a microphone, joystick, game pad, satellite dish, scanner, video camera, depth camera, or the like. In a preferred embodiment, the user enters information into the computing device using an input device 42 that comprises a touch screen, such as touch screens commonly found on tablet computers (e.g., an iPad® 2). These and other input devices are often connected to the processing unit 21 through an input/output (I/O) interface 46 that is coupled to the system bus 23, but may be connected by other types of interfaces, including a serial port, parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feedback game controller).

The computing device 12 may operate in a networked environment using logical connections (wired and/or wireless) to one or more remote computers, such as remote computer 49. These logical connections are achieved by a communication device coupled to or a part of the computing device 12 (as the local computer). Implementations are not limited to a particular type of communications device or interface.

The remote computer 49 may be another computer, a server, a router, a network PC, a client, a memory storage device, a peer device or other common network node or device, and typically includes some or all of the elements described above relative to the computing device 12. The remote computer 49 may be connected to a memory storage device 50. The logical connections depicted in FIG. 25 include a local-area network (LAN) 51 (wired or wireless) and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network (e.g., a mobile communications network such as 3G, 4G, etc.), or power lines. Such a modem may be connected to the computing device 12 by a network interface (e.g., a serial or other type of port). Further, many laptop or tablet computers may connect to a network via a cellular data modem.

When used in a LAN-networking environment, the computing device 12 may be connected to the local area network 51 through a network interface or adapter 53 (wired or wireless), which is one type of communications device. When used in a WAN networking environment, the computing device 12 typically includes a modem 54, a type of communications device, or any other type of communications device for establishing communications over the wide area network 52 (e.g., the Internet), such as one or more devices for implementing wireless radio technologies (e.g., GSM, etc.).

The modem 54, which may be internal or external, is connected to the system bus 23 via the I/O interface 46. The modem 54 may be configured to implement a wireless communications technology (e.g., mobile telecommunications system, etc.). In a networked environment, program modules depicted relative to the personal computing device 12, or portions thereof, may be stored in the remote computer 49 and/or the remote memory storage device 50. It is appreciated that the network connections shown are exemplary and other means of and communications devices or interfaces for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A computer-implemented method for testing macular visual acuity, comprising:
    displaying a first set of objects on a display of a computing device, the first set of objects including at least three objects, exactly one object in the first set objects being different from the other of the objects in the first set, wherein recognition of the difference between the one different object and the other of the objects is indicative of a user's visual acuity;

receiving input from the user via a user input device of the computing device indicating a selection of one of the objects in the first set of objects;

determining whether the user correctly selected the one different object from the first set of objects; and assessing the user's visual acuity based on the selections of the user.

2. The computer-implemented method of claim 1, further comprising:

capturing an image of the user using an image capture device of the computing device;

determining the distance between the display of the computing device and the user based on the captured image; and providing an instruction to the user to either increase or decrease his or her distance from the display based on the determined distance.

3. The computer-implemented method of claim 1, further comprising: subsequent to displaying the first set of objects on the display, displaying a second set of objects on the display of the computing device, the second set of objects including at least three objects, exactly one object in the second set objects being different from the other of the objects in the second set, wherein recognition of the difference between the one different object in the second set and the other of the objects in the second set is indicative of a user's visual acuity;

receiving input from the user via the user input device of the computing device indicating a selection of one of the objects in the second set of objects; and determining whether the user correctly selected the one different object from the second set of objects.

4. The computer-implemented method of claim 3, wherein a characteristic of one or more of the objects in the second set of objects displayed on the display is dependent on whether the user correctly selected the one different object from the first set of objects.

5. The computer-implemented method of claim 1, wherein the computing device comprises a tablet computer and the user input device comprises a touch screen of the tablet computer.

6. The computer-implemented method of claim 1, further comprising:

measuring ambient light level; and adjusting a brightness level of the display dependent on the measured ambient light level.

7. The computer-implemented method of claim 1, further comprising:

measuring ambient light level using the computing device; and providing a notification instructing the user to adjust the ambient light level.

8. The computer-implemented method of claim 1, further comprising:

transmitting data relating to the user's visual acuity to an external computing device.

9. The computer-implemented method of claim 8, further comprising storing the data on the external computing device, and analyzing the data to detect presence of an eye condition.

10. The computer-implemented method of claim 9, further comprising sending a notification from the external computing device to a computing device over a network indicative of the detected eye condition.

11. The computer-implemented method of claim 1, wherein the objects in the first set of objects comprise Vernier acuity targets.

12. The computer-implemented method of claim 1, further comprising, prior to displaying the first set of objects, displaying a set of differently-sized objects on the display, and receiving a selection of an object in the set of differently-sized objects via the user input interface indicating the smallest object in the set of differently-sized objects that is perceptible by the user, wherein the size of the objects in the first set of objects corresponds with the size of the selected object in the set of differently-sized objects.

13. The computer-implemented method of claim 1, further comprising displaying a score on the display based on the number of correct selections by the user.

14. The computer-implemented method of claim 1, wherein the one object in the first set objects is different in size from the other of the objects in the first set.

15. A computer-implemented method for testing macular visual acuity, comprising:

displaying a fixation location indicator on a display of a computing device configured for fixation thereon by a user;

simultaneously and briefly displaying on the display a fixation pattern at the location of the fixation location indicator and at least two pericentral patterns spaced apart from the fixation pattern, wherein one of the pericentral patterns is a correct choice pericentral pattern that is different from the other of the pericentral patterns;

receiving input from the user via a user input device indicating a selection of one of the pericentral patterns;

determining whether the user selected the correct choice pericentral pattern; and recording whether the user selected the correct choice pericentral pattern in a data storage.

16. The computer-implemented method of claim 15, wherein the fixation pattern is positioned on the display near a periphery thereof.

17. The computer-implemented method of claim 15, further comprising:

capturing an image of the user using an image capture device of the computing device;

determining the distance between the display of the computing device and the user based on the captured image; and providing an instruction to the user to either increase or decrease his or her distance from the display based on the determined distance.

18. The computer-implemented method of claim 15, wherein the computing device comprises a tablet computer and the user input device comprises a touch screen of the tablet computer.

19. The computer-implemented method of claim 15, further comprising:

measuring ambient light level; and adjusting a brightness level of the display dependent on the measured ambient light level.

20. The computer-implemented method of claim 15, further comprising:

measuring ambient light level using the computing device; and providing a notification instructing the user to adjust the ambient light level.

21. The computer-implemented method of claim 15, further comprising:

transmitting data relating to the user's visual acuity to an external computing device.

22. The computer-implemented method of claim 21, further comprising storing the data on the external computing device, and analyzing the data to detect presence of an eye condition.

23. The computer-implemented method of claim 22, further comprising sending a notification from the external computing device to a computing device over a network indicative of the detected eye condition.

24. The computer-implemented method of claim 15, wherein the fixation pattern and the at least two pericentral patterns comprise Vernier acuity targets.

25. The computer-implemented method of claim 15, wherein the correct choice pericentral pattern comprises the same pattern as the fixation pattern, and the other of the pericentral patterns comprises a different pattern than the fixation pattern.

26. The computer-implemented method of claim 15, wherein the correct choice pericentral pattern comprises a different pattern than the fixation pattern, and the other of the pericentral patterns comprises the same pattern as the fixation pattern.

27. A system for testing macular visual acuity, comprising:
a display;
a user input device; and
a computer coupled to the display and the user input device, and configured to: simultaneously and briefly display on the display a fixation pattern and at least two pericentral patterns, wherein one of the pericentral patterns is a correct choice pericentral pattern that is different from the other of the pericentral patterns; receive input from the user via the user input device indicating a selection of one of the pericentral patterns; and determine whether the user selected the correct choice pericentral pattern.

28. The system of claim 27, wherein the correct choice pericentral pattern comprises the same pattern as the fixation pattern, and the other of the pericentral patterns comprises a different pattern than the fixation pattern.

29. The system of claim 27, wherein the correct choice pericentral pattern comprises a different pattern than the fixation pattern, and the other of the pericentral patterns comprises the same pattern as the fixation pattern.

30. The system of claim 27, further comprising:
a camera operatively coupled to the computer configured to monitor the ambient light level of the environment of the system, wherein the computer is configured to adjust the brightness of the display dependent on the monitored ambient light level.

31. The system of claim 27, further comprising:
a camera operatively coupled to the computer configured to monitor the ambient light level of the environment of the system, wherein the computer is configured to display a message on the display providing an instruction to the user to adjust the ambient light level of the environment.

32. The system of claim 27, further comprising:
a communications interface coupled to the computer and configured to communicate with an external computer system using wired or wireless communication.

33. The system of claim 27, further comprising:
a camera operatively coupled to the computer configured to capture an image of the user, wherein the computer is configured to determine the distance between the display and the user based on the captured image, and to provide an instruction to the user to either increase or decrease his or her distance from the display based on the determined distance.

34. The system of claim 27, wherein the system comprises a tablet computer and the user input device comprises a touch screen of the tablet computer.

35. The system of claim 27, wherein the fixation pattern and the pericentral patterns comprise Vernier acuity targets.

36. The system of claim 27, wherein the computer is further configured to, prior to displaying the fixation pattern and the pericentral patterns, display a set of differently-sized patterns on the display, and receive a selection of one of the differently-sized patterns via the user input interface indicating the smallest patterns in the set of differently-sized patterns that is perceptible by the user, wherein the size of the fixation pattern and the pericentral patterns corresponds with the size of the selected pattern in the set of differently-sized patterns.

37. The system of claim 27, wherein the fixation pattern is positioned on the display near a periphery thereof.

38. A non-transitory computer-readable medium encoded with computer executable instructions, which when executed, performs a method comprising:
displaying a first set of objects on a display of a computing device, the first set of objects including at least three objects, exactly one object in the first set objects being different from the other of the objects in the first set, wherein recognition of the difference between the one different object and the other of the objects is indicative of a user's visual acuity;
receiving input from the user via a user input device of the computing device indicating a selection of one of the objects in the first set of objects;
determining whether the user correctly selected the one different object from the first set of objects; and
assessing the user's visual acuity based on the selections of the user.

39. The non-transitory computer-readable medium of claim 38, wherein the method further comprises:
capturing an image of the user using an image capture device of the computing device;
determining the distance between the display of the computing device and the user based on the captured image; and
providing an instruction to the user to either increase or decrease his or her distance from the display based on the determined distance.

40. The non-transitory computer-readable medium of claim 38, wherein the method further comprises: subsequent to displaying the first set of objects on the display, displaying a second set of objects on the display of the computing device, the second set of objects including at least three objects, exactly one object in the second set objects being different from the other of the objects in the second set, wherein recognition of the difference between the one different object in the second set and the other of the objects in the second set is indicative of a user's visual acuity;
receiving input from the user via the user input device of the computing device indicating a selection of one of the objects in the second set of objects; and
determining whether the user correctly selected the one different object from the second set of objects.

41. The non-transitory computer-readable medium of claim 40, wherein a characteristic of one or more of the objects in the second set of objects displayed is dependent on whether the user correctly selected the one different object from the first set of objects.

42. The non-transitory computer-readable medium of claim 38, wherein the computing device comprises a tablet computer and the user input device comprises a touch screen of the tablet computer.

43. The non-transitory computer-readable medium of claim 38, wherein the method further comprises:
measuring ambient light level; and
adjusting a brightness level of the display dependent on the measured ambient light level.

44. The non-transitory computer-readable medium of claim 38, wherein the method further comprises:
measuring ambient light level using the computing device; and
providing a notification instructing the user to adjust the ambient light level.

45. The non-transitory computer-readable medium of claim 38, wherein the method further comprises:
transmitting data relating to the user's visual acuity to an external computing device.

46. The non-transitory computer-readable medium of claim 45, wherein the method further comprises storing the data on the external computing device, and analyzing the data to detect presence of an eye condition.

47. The non-transitory computer-readable medium of claim 46, wherein the method further comprises sending a notification from the external computing device to a computing device over a network indicative of the detected eye condition.

48. The non-transitory computer-readable medium of claim 38, wherein the objects in the first set of objects comprise Vernier acuity targets.

49. The non-transitory computer-readable medium of claim 38, wherein the method further comprises, prior to displaying the first set of objects, displaying a set of differently-sized objects on the display, and receiving a selection of an object via the user input interface indicating the smallest object in the set of differently-sized objects that is perceptible by the user, wherein the size of the objects in the first set of objects corresponds with the size of the selected object in the set of differently-sized objects.

50. The non-transitory computer-readable medium of claim 38, wherein the method further comprises displaying a score on the display based on the number of correct selections by the user.

51. The non-transitory computer-readable medium of claim 38, wherein the one different object in the first set objects differs from the other of the objects in the first set of objects in one of color and gray level.

52. A computer-implemented method for providing a video game for testing macular visual acuity, the method comprising:
testing central visual acuity by executing a plurality of central visual acuity rounds of the video game, each central visual acuity round comprising:
displaying at least three central acuity targets on a display of a computing device, one of the at least three central acuity targets being different from the other of the central acuity targets, wherein recognition of the difference between the one different central acuity target and the other central acuity targets is indicative of a user's central visual acuity;
receiving a selection of one of the central acuity targets from the user via a user input device of the computing device;
determining whether the user correctly selected the one different central acuity target from the central acuity targets; and
assessing the user's central visual acuity based on the selection of the user;
testing pericentral visual acuity by executing a plurality of pericentral visual acuity rounds of the video game, each pericentral visual acuity round comprising:
displaying a fixation location indicator on the display of the computing device configured for fixation thereon by a user;
simultaneously and briefly displaying on the display a fixation target at the location of the fixation location indicator and at least two pericentral acuity targets spaced apart from the fixation target, wherein one of the pericentral acuity targets is a correct choice pericentral acuity target that is different from the other of the pericentral acuity targets, the correct choice pericentral acuity target being positioned relative to the fixation target such that perception of the correct choice pericentral acuity target is indicative of the user's visual acuity at a location on an acuity map;
receiving a selection of one of the pericentral acuity targets from the user via the user input device;
determining whether the user selected the correct choice pericentral acuity target; and
recording whether the user selected the correct choice pericentral acuity target in a data storage; and
generating a visual acuity map based on the user's selections during the plurality of central acuity and pericentral acuity rounds, wherein in the visual acuity map is divided into a plurality of locations, and each of the plurality of locations is tested by at least one of the central acuity or pericentral acuity rounds of the video game.

53. The computer-implemented method of claim 52, wherein, during each of the central acuity rounds, a characteristic of the central acuity targets displayed on the display is dependent on the user's selection of a central acuity target in a previous central acuity round.

54. The computer-implemented method of claim 52, wherein, during each of the pericentral acuity rounds, a characteristic of the fixation target and the pericentral acuity targets displayed on the display is dependent on the user's selection of a pericentral acuity target in a previous pericentral acuity round.

55. The computer-implemented method of claim 52, wherein a characteristic of the central acuity targets and the pericentral acuity targets is initially selected based on the user's previous visual acuity test results.

56. The computer-implemented method of claim 52, wherein a characteristic of the central acuity targets and the pericentral acuity targets is initially selected based on visual acuity information of a normal population.

57. The computer-implemented method of claim 52, further comprising:
capturing an image of the user using an image capture device of the computing device;
determining the distance between the display of the computing device and the user based on the captured image; and
providing an instruction to the user to either increase or decrease his or her distance from the display based on the determined distance.

58. The computer-implemented method of claim 52, wherein the computing device comprises a tablet computer and the user input device comprises a touch screen of the tablet computer.

59. The computer-implemented method of claim 52, wherein the central acuity targets and the pericentral acuity targets comprise Vernier acuity targets.

* * * * *